United States Patent [19]
Gevins et al.

[11] Patent Number: 5,724,987
[45] Date of Patent: Mar. 10, 1998

[54] NEUROCOGNITIVE ADAPTIVE COMPUTER-AIDED TRAINING METHOD AND SYSTEM

[75] Inventors: Alan Gevins; Harrison Leong; Isabel Sam-Vargas; Michael Smith, all of San Francisco, Calif.

[73] Assignee: Sam Technology, Inc., San Francisco, Calif.

[21] Appl. No.: 504,653

[22] Filed: Jul. 20, 1995

Related U.S. Application Data

[63] Continuation-in-part of Ser. No. 183,621, Jan. 19, 1994, Pat. No. 5,447,166, which is a continuation-in-part of Ser. No. 766,826, Sep. 26, 1991, Pat. No. 5,295,491.

[51] Int. Cl.$^6$ .................................. A61B 5/0476
[52] U.S. Cl. .............................. 128/731; 434/258
[58] Field of Search ........................ 128/731, 732; 434/326, 262, 118, 238, 258

[56] References Cited

U.S. PATENT DOCUMENTS

| | | |
|---|---|---|
| 5,295,491 | 3/1994 | Gevins . |
| 5,447,166 | 9/1995 | Gevins . |

*Primary Examiner*—Scott M. Getzow
*Attorney, Agent, or Firm*—Eliot S. Gerber

[57] ABSTRACT

A computer-aided training system uses electroencephalograms (EEGs) recorded from the trainee's scalp to alter the training protocol being presented by the computer, for example to present a new task to the trainee when he or she has mastered and automatized the current task. The index of the trainee's skill mastery and automatization is determined by analysis of the EEG using mathematical classification functions which distinguish different levels of skill acquisition. The functions are computed by computer neural networks and consist of a combination of EEG and other physiological variables which specifically characterize a trainee's level of focused attention and neurocognitive workload and his or her neurocognitive strategy. The functions are derived either for a group of trainees, or each trainee individually, performing a battery of one or more standard training tasks while wearing an EEG hat.

50 Claims, 9 Drawing Sheets

Initial Practce  Highly Skilled

−2.5     2.5

NEUROCOGNITIVE ADAPTIVE COMPUTER-AIDED TRAINING METHOD AND SYSTEM

This application is a continuation-in-part application based in part on application Ser. No. 08/183,621, Filed Jan. 19, 1994, Neurocognitive Adaptive Computer Interface Method and System Based on On-Line Measurement of the User's Mental Effort, now U.S. Pat. No. 5,447,166 issued Sept. 5, 1995 which is a continuation-in-part application based in part on application Ser. No. 07/766,826 for "Non-Invasive Human Neurocognitive Performance Testing Method and System", filed Sept. 26, 1991 now U.S. Pat. No. 5,295,491, issued Mar. 22, 1994.

This invention was made with Government Support under contract numbers F49620-92-C-0013 and F49620-94-C-0075 awarded by the Air Force Office of Scientific Research. The Government has certain rights in this invention.

BACKGROUND OF THE INVENTION

1. Field of the Invention

The present invention relates to an adaptive computer-aided training method using neuroelectric signals recorded from the trainee's scalp, i.e., electroencephalograms (EEGs).

2. Description of Related Art

The use of computer-aided training is rapidly expanding in education, industry and government because of its ability to present material at a pace directed by the trainee, as compared with traditional instruction in which everyone in the class receives the same material at the same rate. This growth in automated training derives from the fact that over 95% of trainees with private human tutors do better than the trainee in a standard classroom. In order to make these educational benefits of tutoring more widely available, a substantial investment has been directed to the problem of creating computer-based training systems that can approximate the effectiveness of human tutors. Although in some cases such intelligent tutoring systems have also demonstrated higher effectiveness in transmitting knowledge and skills over that afforded by conventional classroom methods, the margin of improvement has heretofore been significantly lower than that provided by personalized human training. A large part of the discrepancy in effectiveness between human and automated tutoring probably derives from the more intimate knowledge a human tutor has about a trainee's mental state. A computer-aided training system can be endowed with a trainee model that describes the general parameters of human capacities. Similarly, that model can be enriched by eliciting preference information from the trainee or by using the trainee's task performance to draw inferences about domain-specific knowledge or skill level. However, in addition to these types of trainee information, a skilled human tutor can also gauge whether a trainee is expert or naive, challenged or bored, engaged or distracted, motivated or indifferent, and, perhaps, what type of cognitive style or strategy the trainee is employing. That is, a skilled human teacher has the ability to utilize subtle interpersonal cues to infer information about a trainee's mental state, and he or she can use this information to dynamically modulate the training session to accommodate or modify that state.

The lack of on-line knowledge of the trainee's mental state is thus a major limitation in computer-aided training systems which prevents them from optimally adapting the material to the trainee's needs. Other than observing long samples of behavior, a computerized training program has no way to infer whether a particular subtask skill or area of expertise is adequately familiar or whether the trainee would benefit from more practice. Indeed, a central issue in the development of computerized training systems is the question of how to assess when and to what degree learning has occurred. Complex tasks may be said to lie along a continuum which runs from more knowledge-based to more performance-based. For example, tasks such as electronic troubleshooting or medical diagnosis are very knowledge-based, whereas tasks such as cutting a diamond or repairing a jet engine tend to be much more performance-based. While both types of tasks require a certain amount of knowledge in order to perform them properly, knowledge-based tasks tend to require more depth-of-knowledge and conscious effort on the part of the individual performing the task. In contrast, more performance-based tasks require an assimilation of the required knowledge to the point where less conscious effort is required for superior task performance. Such an assimilation, or "automatization," of the task allows the individual to perform other functions at the same time ("multitasking"), and renders task performance highly reliable under stress. For example, a common instance of the transition to automatic performance occurs when learning to drive an automobile. At first, the task requires a great deal of conscious attention. After sufficient practice, accomplished drivers are capable of simultaneously performing several other tasks while driving, such as carrying on conversations, operating a stereo, and so on. Many situations, both in and out of the workplace, require this sort of multitasking. In air-to-air combat, for example, it is important for the pilot to have automated the mechanics of flying the airplane ("stick-and-rudder" skills) in order to free the pilot's conscious attention for concentrating on strategy and tactics. Thus, one important benefit of automatizing components of a task is that cognitive resources are freed up for other, non-automatized task components. This phenomena has been theoretically accounted for as a relegation of task control to pre-conscious nervous system control. Recent Positron Emission Tomography (PET) brain-imaging data has supported this notion, showing that less cortical blood flow (implying less cortical activation) is observed after practice on complex tasks (e.g., Haier et al., 1992; Raichle et al., 1994; Risberg, 1977). While this is interesting scientific information, large brain scanners such as those used in Positron Emission Tomography or Magnetic Resonance Imaging (MRI), are not practical to use in computer-aided training systems because of their requirement for immobilization of the trainee in a very large and expensive brain scanner, and their costs of operation.

A popular training strategy, called part task training, trains a person in the individual components comprising a complex task. Any applied skill of reasonable complexity is likely to involve both consistent and inconsistent components. Consistent components are those aspects of the task which are performed in a routinized manner across trials, and practice on such components has been shown to produce substantial improvements in performance as automatic processing develops (e.g., 98% reduction in visual search comparison rates). Automatization of consistent components may be facilitated during training by allowing trainees to attend fully to the isolated components. In contrast, inconsistent components vary across trials, use only controlled processing, and show little improvement in performance with practice (e.g., no change in letter search performance over four months of training). For consistent task components, practice greatly reduces the amount of mental effort required to perform the component, allowing controlled processing to be allocated to other task components. That is, when trainees have already developed automatic processes to perform one task component, they can learn to time-share another task (or task component) with little or no deficit in performance. For example, after 20 hours of consistent practice in two search tasks, trainees were able to perform both tasks simultaneously nearly as well as they could perform each separately (Fisk & Schneider). In sum, the acquisition of high-performance skill with practice is assumed to result from the development of automatic processes which are used to perform consistent task components.

According to a commonly accepted model of learning (e.g. Kyllonen & Christal, 1989), skill acquisition can be seen as a progression that begins with encoding declarative (factual) knowledge, that continues with learning procedural (action-centered) knowledge and skill, and, with sufficient practice, that leads to the development of habits or automatized behaviors that don't require conscious deliberation. In other words, skills are initially acquired as a set of declarative facts or rules, then proceduralized into "action recipes," and, with extended practice, these action recipes may in turn become gradually less demanding of cognitive resources. According to this model, progression through the three stages of skill acquisition can be tracked by monitoring three classes of performance measures. Early on, during declarative knowledge acquisition, measurements of task accuracy improve rapidly to some asymptotic level. Next, during procedural knowledge/skill acquisition, measurements of task latency gradually decline to some limiting level. Finally, the amount of attentional resources (as measured indirectly by secondary task performance) required by the target task begins to decrease (Carlson, Sullivan, & Schneider, 1989).

While this model captures much of the flavor of task acquisition, it neglects some important aspects of skilled performance. Everyday experience provides ample evidence that some rote components of complex tasks, such as classifying complex recurring patterns of information or responding appropriately to stimuli of a particular class, become automatic with extended practice. However, task performance at the level of expertise of a concert violinist, a chess master, or a professional athlete can be presumed to require a good deal of focused attention. Presumably such highly skilled individuals have automatized the routine aspects of their craft, and their major attentional task becomes one of selectively concentrating on the less routine aspects of task performance. Thus, mastery of a complex neurocognitive skill might better be conceived of as a process in which one automatizes lower-order aspects of task performance, while also developing a more sophisticated ability to concentrate attention on higher-order aspects.

OBJECTIVES AND FEATURES OF THE INVENTION

Thus, there currently is no unobtrusive way to obtain information about whether a trainee has mastered learning a procedure or skill to the point where concentration has become more efficient and consistent and with reduced overall mental effort. There is also no unobtrusive method for determining what strategy the trainee is using to perform the task, for example whether he or she is verbalizing the procedure or picturing it. Current obtrusive methods for obtaining this information involve querying the trainee about his or her mental state, or asking him or her to simultaneously perform some other irrelevant secondary task, such as tapping a foot switch, while performing the task they are learning. Besides distracting from the flow of the training session, querying the trainee can be inaccurate since people are not always aware of their mental state. Similarly, having to perform an irrelevant secondary task can be distracting and can interfere with learning the primary task.

What is therefore needed is a system using a computer to assess the degree of mastery and automatization of a trainee's acquisition of a skill, as a result of training, by unobtrusively measuring the increase in focused attention and decrease in overall level of mental effort. With this information, the computer system could then determine the optimal time to advance the trainee to the next task to be learned or to the next required level of task performance. Additionally, it would be useful for the system to know what sort of strategy the trainee is using to perform the task. We call this type of computer-aided training system a "Sympathetic Neurocognitive Adaptive Computer-Aided Training System". Such a system would facilitate the acquisition of new skills by allowing the computer system to rapidly adapt the information presented to match the trainee's level of proficiency. Similarly, in situations where the trainee is being presented with information but is not required to respond, knowledge about the trainee's attentional state and level of mental effort could be used to adjust the presentation of information to maintain an optimal level of attention and comprehension.

In the following, the term "neurocognitive" refers to those mental functions for which physiological indices can be measured. The terms "focused attention" and "concentration" are used synonymously. The term "neurocognitive workload" refers to the level of neural activation associated with mental effort and is measured physiologically as described in U.S. patent application Ser. No. 08/183,621. Filed Jan. 19, 1994, Neurocognitive Adaptive Computer Interface Method and System Based on On-Line Measurement of the User's Mental Effort, now U.S. Pat. No. 5,447, 166. The phrases "skill acquisition, mastery and automatization" and "skill acquisition and automatization" are used interchangeably to denote a high degree of skill mastery in which a high level of performance and focused attention can be maintained with a relatively low level of task-specific neurocognitive workload. The term "neurocognitive strategy" refers to the strategy a trainee uses to perform a task and is characterized by a particular pattern of regional utilization of brain areas, ie. differential degrees of utilization of brain systems involved with perception, action, and cognition including, but not limited to: the anterior cingulate, planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsolateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

It is thus an objective of the current invention to provide a method and system that uses realtime measurements of brain electrical signals to measure a trainee's degree of focused attention, neurocognitive workload and neurocognitive strategy in order to provide a computer-aided training system with information concerning a trainee's level of skill acquisition, mastery and automatization of performance of a task, thereby helping to accelerate the process of skill acquisition and automatization by more rapidly adapting the training protocol to the level of expertise of the trainee.

It is an objective of the present invention to provide a method and system for measuring the degree of a trainee's level of focused attention, neurocognitive workload and neurocognitive strategy using neuroelectric (EEG) with or without other physiological signals (e.g., eye, scalp or facial muscle and heart activity, and respiration) in order to provide the computer system with information about whether and how the trainee has mastered and automatized the task to be learned.

It is a further objective of the present invention to obtain the metric of skill acquisition and automatization noninvasively and on-line while the trainee is actively interacting with the computer-aided training system or while the trainee is passively receiving information from the computer-aided training system.

It is a further objective of the present invention to obtain a trainee-specific calibration for the metrics of focused attention, neurocognitive workload and neurocognitive strategy non invasively using a combination of stimuli, behavioral tasks, physiological measures and neuroelectric signals to train the computer to recognize the different levels of skill acquisition, mastery and automatization for each individual trainee. This type of calibration process provides the basis for deriving trainee-specific mathematical functions for relating patterns of neuroelectric activity, with or without other physiological measures, to level of focused attention, neurocognitive workload and neurocognitive strategy in order to infer the degree of a trainee's skill acquisition, mastery and automatization.

It is a further objective of the present invention to obtain a generic trainee-independent calibration for the metrics of focused attention, neurocognitive workload and neurocognitive strategy non invasively using a combination of stimuli, behavioral tasks, physiological measures and neuroelectric signals to train the computer to recognize the different levels of skill acquisition, mastery and automatization for a group of people. This type of calibration process provides the basis for deriving trainee-independent mathematical functions for relating patterns of neuroelectric activity, with or without other physiological measures, to the level of focused attention, neurocognitive workload and neurocognitive strategy in order to infer the degree of a trainee's skill acquisition and automatization. These functions can then be applied to a previously untested trainee to measure his or her degree of skill acquisition and automatization while learning a task.

It is still a further objective of the present invention to obtain measures of level of focused attention, neurocognitive workload and neurocognitive strategy noninvasively using a combination of neuroelectric and/or physiological signals for an individual trainee without prior calibration data either from that individual or from a group of people by comparing values of these data with thresholds derived from prior studies.

It is a feature of the present invention to provide a computer aided training system which is sympathetic and responsive to the trainee's level of skill acquisition, mastery and automatization by adapting its training program to optimally stress the neurocognitive workload of the trainee as well as to encourage an optimal neurocognitive learning strategy for the task at hand. For example, the system can advance to the next task or require a faster or higher level of task performance during a multimedia training session if it determines the trainee has mastered and automatized the current task by comparing the trainee's current level of focused attention, neurocognitive workload and neurocognitive strategy with the mathematical functions derived during the calibration process, or with thresholds derived from prior studies. Additionally, the computer can change the distribution of information between visual and auditory modalities, or, for the visual modality, between linguistic and graphical types of information display, if the trainee's neurocognitive strategy differs from the optimal neurocognitive strategy for the task at hand.

Other features of the present invention include the ongoing measurement of combinations of alpha and beta (13–26 Hz) band EEG activity and temporalis, occipitalis and frontalis muscle activity to measure neurocognitive workload, measurement of theta band EEG activity from the anterior cingulate and prefrontal cortex to measure level of focused attention, and regional patterns of theta, alpha and beta band EEG activity to measure neurocognitive strategy, as well as measurement of other physiological signals such as eye movements, using two or more electrodes placed on the body surface in order to assess the level of a trainee's skill acquisition and automatization.

Yet another feature of the present invention is the processing of the neuroelectric and other physiological signals in time intervals ranging from 100 milliseconds to several hours to derive measures of skill acquisition, mastery and automatization which are transmitted to the same or a different computer in order to adjust the operation of the computer or simply to record the trainee's responses.

SUMMARY OF THE INVENTION

In accordance with the present invention, there is provided a novel method and system for measuring the level of focused attention, neurocognitive workload and neurocognitive strategy in order to provide the computer with on-line information about the trainee's level of mastery and automatization of a task being learned. These data are then used by the computer system to optimally adapt the information presented by the computer to match the current level of skill acquisition, mastery and automatization of the trainee.

The main advantage of the "Sympathetic Neurocognitive Adaptive Computer-Aided Training System" is that it automatically adapts the information presented to the trainee by taking into consideration the trainee's degree of skill acquisition, mastery and automatization as inferred from the trainee's level of focused attention, neurocognitive workload and neurocognitive strategy. This differs from other computerized training systems where the system responds only to the trainee's specific, consciously directed behavioral responses.

The system operates as follows: As the trainee performs a task under the guidance of a computer-aided training system, her or his neuroelectric (EEG) signals, possibly with other physiological signals, are measured and contaminating artifacts are removed. Mathematical features are then computed from these signals according to formulas determined either from the trainee's or a group of people's prior training data, or by reference to general patterns associated with learning from prior research. The formulas determine an overall score related to the trainee's degree of skill acquisition, mastery and automatization, as well as scores which characterize the trainee's neurocognitive strategy. The scores are then used to adjust the training protocol in order to maintain optimal levels of neurocognitive workload and focused attention and to encourage utilization of an optimal neurocognitive strategy. In the case of a trainee learning how to control a complex system such as an airplane, the system can determine that a component task, such as steering the plane, has been mastered if the overall degree of skill acquisition and automatization score surpass a selected high level threshold. Conversely, if the score is below a low level threshold, the system can continue to give the trainee more exercises of the same task. The system can also adjust the training material presented to the trainee based on how the trainee's neurocognitive strategy departs from an optimal standard for the task being learned. For example, if a trainee is learning how to make a banked turn in an airplane simulator and her or his right parietal and right prefrontal spatial processing cortical brain areas are insufficiently activated, while her or his left parietal and left prefrontal linguistic cortical brain areas are excessively activated, the system can infer that the trainee is excessively talking to herself or himself about how to make the turn rather than simply visualizing the movement of the plane in three dimensions. It would then instruct the trainee on how to visualize the maneuver. In the case of a trainee performing an attention training exercise, the system can present information at the instant at which the trainee's preparatory attention is optimal as determined by measuring the level of focused attention, neurocognitive workload and neurocognitive strategy just prior to presentation of information. Alternatively, it could wait until the trainee was not paying attention to present the information in order to demonstrate the detrimental effect of allowing focused attention to lapse.

The dual components of task mastery (automating routine aspects and concentrating on less routine aspects) appear to be reflected in changes in the spectral composition of the ongoing EEG, ie. power at different frequencies of the trainee's brainwaves. For example, it has long been observed that the strength of EEG signals in the alpha (7–13 Hz) band are inversely related to the difficulty of a cognitive task. We have determined that when individuals develop some degree of expertise in performance of specific complex computer-based tasks, alpha-band activity increases across widespread regions of the scalp. This is consistent with the notion that task performance requires less cognitive resources overall when subjects are highly practiced. Conversely, the strength of theta (3–7 Hz) band EEG signals recorded at frontal electrodes has been shown to increase in more difficult tasks, and is presumed to be associated with a cognitive state of focused attention. We have also found that when individuals practice specific complex computer-based tasks, frontal theta alpha-band also increases. This implies that subjects are learning to focus attention more effectively on those components of task performance that do not become automatic.

BRIEF DESCRIPTION OF THE DRAWINGS

Other objectives and features of the present invention will be apparent from the following detailed description, taken in conjunction with the accompanying drawings. In the drawings.

DETAILED DESCRIPTION OF THE INVENTION

Figure 1:
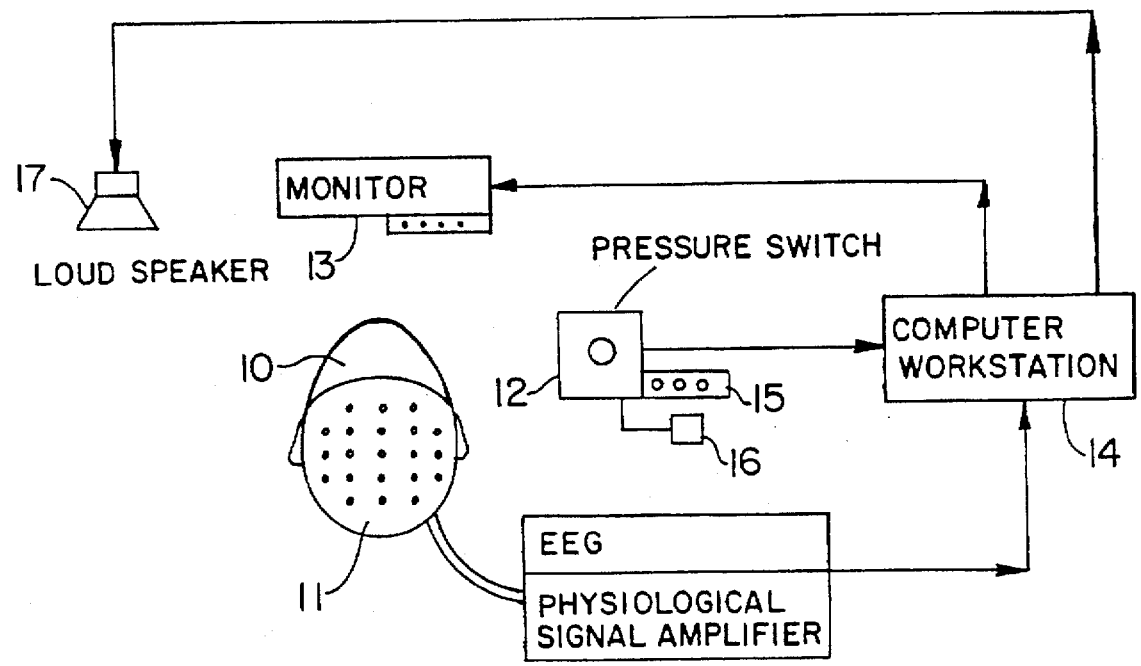
FIG. 1 is a schematic diagram of the system of the present invention.

The present invention is illustrated in FIG. 1. As shown therein, a human trainee 10, whose head is illustrated, wears a cloth hat 11, or headset having electrode leads which contact the scalp of the trainee. The leads detect the trainee's weak analog brain waves and also the electrical activity of his eyes and scalp muscles. Electrodes or other sensors are connected by wires to the hat attach to the chest, back, limbs, neck or face to record other physiological signals including heart activity, respiration, facial or limb muscle activity, eye activity, or skin conductance. A suitable EEG hat is described in the inventor's U.S. Pat. No. 5,038,7832, issued Aug. 13, 1991 and incorporated by reference herein. The hat has preferably 8–64 independent electrodes, although fewer or more electrodes may be used. The brain waves are amplified, preferably as described in the U.S. Pat. No. 5,038,7832, and artifacts detected and removed, for example, as described in U.S. Pat. No. 4,736,751 issued Apr. 12, 1988 and entitled "Brain Wave Source Network Location Scanning Method And System", and as described in U.S. patent application Ser. No. 08/216,256, filed Mar. 22, 1994. and entitled "Adaptive Interference Canceller for EEG Movement and Eye Artifacts," which are incorporated by reference herein.

Other physiological signals are detected and measured, for example, as follows: Eye movements and blinks are measured with EEG electrodes placed near the eyes, preferably above and below one eye for vertical movements and blinks, and on the nasion and outer cathus of one eye for horizontal movements (electroculogram or EEG). The amplifier response to such eye movements and blinks is similar to that for EEG, except that gain is reduced by a factor of 2 to 25. Alternatively, eye movements and blinks may be measured with an optoelectric device which measures the reflection of infrared light from the margins between the iris and sclera on either side of the pupil. Scalp or facial muscle potentials (electromyogram or EMG) are measured with EEG electrodes placed over scalp muscles or on the face, with a bandpass of from approximately 36 to 100 Hz. Heart activity (electrocardiogram or ECG) is measured with conventional ECG electrodes placed appropriately on the upper chest, limbs or neck. Amplifier response is similar to that for EEG, except that gain is reduced by a factor of 2 to 10. Skin conductance response (SCR) is obtained from the voltage generated by an alternating current of roughly 10 microamps run through two electrodes placed appropriately on the trainee's forehead, fingers, palm or armpit. Amplifier response is similar to that for EEG, except that gain is reduced by a factor of 10 to 100. Respiration is measured by a nasal thermistor or an electrically resistive stretch device placed around the upper chest. Changes in resistance are indicated by the amplifier output of a bridge circuit with a regulated voltage input.

Using time segments of the decontaminated data that are 100 milliseconds or more, various parameters are extracted which are specific for each type of physiological signal and which have been found to discriminate learning, as described below. For heart activity, the parameter is heart rate. For respiration, the parameter is respiration rate and amplitude. For eye activity, the parameters include but are not limited to eye blink rate and eye blink duration. For scalp or limb muscle activity, the parameter is the root mean square value of the signal from each of the muscle sensors. For brain electrical activity, the parameters include but are not limited to power at the peak frequency, power of individual components and whole band power in the 3–7 Hz ("theta"), 7–13 Hz ("alpha") and 13–26 Hz ("beta") bands, and integrated power from 30–50 Hz ("muscle"), between-channel coherence, correlation, crosspower or covariance in these bands (for example, as described in U.S. Pat. No. 4,736,751). Prior to computing these parameters, brain electrical activity may be spatially sharpened using an algorithm described in U.S. Pat. No. 5,331,970. The parameters are computed every n milliseconds where n is the duration of a time segment and can typically range from 100 to 100,000 depending on the training application. Time segments can overlap each other by 0–75% depending on how often an updated skill acquisition and automatization index is needed. Taken together, all of the described parameters constitute the basic set of variables used to construct mathematical classification functions, as described below, which determine an overall score related to the trainee's degree of skill acquisition, mastery and automatization, as well as scores which characterize the trainee's neurocognitive strategy.

Subsets of the basic variables may optionally be combined using Principal Components analysis to decrease the number and statistical dependence between variables used in constructing the classification functions. The set of submitted variables can be a combination of Principal Components and any of the basic variables described above. Normalizing transforms are applied to these variables as needed. The final step in preparing the data for the classification functions is to compute Z-scores across the data samples as described below, and to organize the variables into separate groupings which characterize levels of focused attention, neurocognitive workload and neurocognitive strategy. Variables used to measure level of focused attention preferably include power at the peak frequency, power of individual spectral components and whole band power in the 3–7 Hz (theta) EEG band recorded from electrodes over the prefrontal cortex. Variables used to measure neurocognitive workload preferably include power at the peak frequency, power of individual spectral components and whole band power in the 7–13 Hz (alpha) and 13–26 Hz (beta) EEG bands recorded from electrodes over the entire cortex, and temporalis, occipitalis and frontalis muscle activity in the 30–50 Hz band. The theta, alpha and beta band variables are further subgrouped into individual cortical areas to measure neurocognitive strategy, ie. the pattern of differential utilization of brain systems involved with perception, action, and cognition including, but not limited to: the anterior cingulate, planum temporale, superior temporal gyrus, Heschl's gyrus and associated structures involved with auditory processing and speech perception; the occipital and inferotemporal cortices and the parieto-occipitotemporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsolateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

There are two aspects of pattern classification analysis, namely training the classification functions and applying the functions. In the former, a mathematical function, preferably a computer neural network, is trained to recognize the stages of skill acquisition and automatization from naive to competent performance to mastery and autorealization. This training can be done either on data from each trainee individually, or on data from a group of people doing a representative sample of calibration training tasks such as the working memory and superdivided attention tasks described in U.S. patent application Ser. No. 08/183,621, Filed Jan. 19, 1994, entitled "Neurocognitive Adaptive Computer Interface Method and System Based on On-Line Measurement of the User's Mental Effort", now U.S. Pat. No. 5,447,166, issued Sep. 5,1995, or other tasks such as described below. In either case, neuroelectric data (with and without other physiologic data) elicited during the course of learning a task(s) define the discrete learning levels to be recognized by the classification functions. In the case of training on data from a group of people, a specific task can be used which new people can then be trained on, eg. learning how to fly a particular model of airplane. Such classification functions are created from neuroelectric measures, with and without other physiologic measures. Preferably using the variables and groupings of variables described above, separate functions can be developed to index levels of focused attention, neurocognitive workload and neurocognitive strategy, or a single function can be developed to index all three processes simultaneously to produce a single index of skill acquisition and automatization. In the former case, the numerical outputs of the focused attention function and at least one of the other two functions are combined into a single index of skill acquisition and automatization. In the latter case, the relative weightings of the three processes within the single function are compared to make inferences about attention, workload and strategy. Regardless of whether group or individual trainee functions are trained, and regardless of how the variables are grouped, each variable input to the functions must first be transformed for each trainee into Z-score variables across the set of data used for training. Data set aside for testing the functions must be separately transformed into z-scores, ie. not mixed with the data used for training. This type of transformation has the effect of removing irrelevant differences in overall scale between variables and between trainees. The transformed data are then labeled as to the level of skill acquisition and input to a computer program embodying a classification function training algorithm, preferably a neural network pattern classification algorithm such as that described in the studies below in which a special case of the algorithm was used to obtain a function which recognized the two extrema of learning, namely initial practice vs. highly skilled task performance. The analysis is preferably extended to handle more than two levels of skill acquisition and automatization, and generalized to generate a continuous index. In the latter case, networks (computer neural networks) are further trained to interpolate between levels. In the process of constructing the networks, the algorithm identifies the best combination of variables for accurately and reliably indexing skill acquisition and automatization. As mentioned above, individual networks so constructed can be combined into larger networks to give overall skill acquisition and automatization indices which combine data from several types of physiological and neuroelectric data, or a single network can be computed from groupings of all the types of variables to produce an overall index.

In the case of classification functions trained on data from a group of people, the functions may optionally be adjusted using a new individual trainee's calibration data to maximize the accuracy and reliability of indexing that trainee's skill acquisition and automatization. The calibration data is gathered from a training task or small set of tasks specifically designed to adequately calibrate a generic network, eg. the working memory an super-divided attention tasks described below. In this case, calibration data are preferably used to adjust a small subset of parameters of the neural network pattern analyzers. The adjustments are made to accommodate the peculiarities of the trainee's neuroanatomy and neurophysiology; i.e., the particular conductive properties of the trainee's tissues, geometry of these tissues, neurodynamical properties of the trainee's brain, and the trainee's functional brain organization. The final step of the function training process is to determine that the functions show significantly high accuracy of classification of levels of skill acquisition and automatization when tested with data not used for training. This is preferably done with a resampling or jacknife procedure as described in the experiments below. If the classification functions are sufficiently accurate, they may be applied to measure the degree of a trainee's skill acquisition and automatization.

Although having specific mathematical functions derived from examples of trainees learning how to perform appropriate tasks produces the best results, it is also possible to determine a trainee's level of skill acquisition and automatization without such a function by comparing his or her data to general patterns associated with training from prior research.

The Sympathetic Neurocognitive Adaptive Computer Training system is then used as follows: A brief, preferably one minute, system initialization period begins when a trainee first starts learning a task; neuroelectric signals, with or without other physiological data, from the initialization period are recorded, artifacts are removed, and the decontaminated signals are processed as described above to derive initial estimates of the statistical distribution of variables needed for the transformation into z scores. After the initialization period is over, the system measures the appropriate data and performs the appropriate computations to measure the variables which characterize the trainee's level of focused attention, neurocognitive workload and neurocognitive strategy. These variables are then transformed into z-scores using the data from the initialization and subsequent periods and input into the previously computed classification functions in order to determine the trainee's degree of skill acquisition and automatization. The information about the level of skill acquisition and automatization is then used to adjust the training protocol in order to maintain optimal levels of neurocognitive workload and focused attention and to encourage utilization of an optimal neurocognitive strategy. For example, if a trainee is learning how to control the flight dynamics of an aircraft, the computer-aided training system can begin to train him or her how to conduct a simultaneous communication task when it determines that the trainee's skill acquisition and automatization score is above a certain threshold. As another example, if a trainee is learning how to make a banked turn in an airplane simulator and her or his right parietal and right prefrontal spatial processing cortical brain areas are insufficiently activated, while her or his left parietal and left prefrontal linguistic cortical brain areas are excessively activated, the system can infer that the trainee is excessively talking to her or himself about how to make the turn rather than simply visualizing the movement of the plane in three dimensions. It would then instruct the trainee on how to visualize the maneuver. As another example, when a trainee answers a question incorrectly during a computerized training protocol, by evaluating the trainee's level of focused attention and neurocognitive workload, the system can determine whether the student was not paying attention or whether she or he was trying hard and simply did not know or understand the material. In the former case, an alerting signal could be presented and then the same material could be repeated. In the latter case, by analyzing the trainee's neurocognitive strategy and comparing it to optimal strategies, the system can determine whether or not the trainee was employing an appropriate strategy to solve the problem. If so, a more detailed explanation of the material which was not understood could be presented. If the trainee was using the wrong strategy for the problem, an explanation of how to go about solving the problem could be presented. For instance, it might be determined that at the time the trainee made an error when answering a question requiring visualization of how the parts of an engine fit together, he was using 75% of his cognitive capacity; visuospatial systems were at 45% of capacity, while verbal encoding and output systems were at 85%. From this information, the system could conclude that the trainee was trying to solve the problem with a verbal strategy which was not efficient for the problem at hand and could present the student with information showing him or her how to use a visuospatial strategy to solve the problem. In still another example in which a trainee is performing an attention training exercise, the system can present information at the instant at which the trainee's preparatory attention is optimal as determined by measuring the level of focused attention, neurocognitive workload and neurocognitive strategy just prior to presentation of information. Alternatively, it could wait until the trainee was not paying attention to present the information in order to demonstrate the detrimental effect of allowing concentration to lapse. In all these examples, information about the trainee's level of skill acquisition and automatization can be used for the purpose of modulating the content, rate, and/or format of the information being presented by a computer-based training system. Analogous sorts of application can be made even when a trainee is passively watching a computer controlled training presentation, as mentioned above.

The following description is of several experiments demonstrating the use of neural network pattern recognition technology to extract physiological indices which discriminate naive from well practiced performance of several different types of tasks, and which discriminate different levels of mental workload.

METHOD AND RESULTS OF EXPERIMENTS

Analysis of Practice Effects in High Load Working Memory Tasks

We examined learning trends in datasets in which trainees practiced complex computer-based working memory tasks for several hours over the course of one or more training sessions. During this period their EEG, as well as eye activity (EOG) and scalp muscle activity (EMG), were recorded from 32-124 channel electrode montages. Data-files were first preprocessed using EEG artifact decontamination algorithms. In these tasks, which are described in U.S. patent application Ser. No. 08/183,621. Filed Jan. 19, 1994, Neurocognitive Adaptive Computer Interface Method and System Based on On-Line Measurement of the User's Mental Effort, now U.S. Pat. No. 5,447,166, issued Sep. 5,1995, stimuli were presented in a continuous sequence and the trainee was required to compare the current stimulus with those earlier in the sequence. Each stimulus was selected from a set of twelve capital letters, and displayed in one of twelve screen positions. In a spatial load condition trainees were required to compare the current stimulus to either a constant stimulus (control task), the immediately preceding stimulus (low load WM task) (Working Memory), the stimulus that occurred two trials ago (intermediate load WM task), or the stimulus that occurred three trials ago (high load WM task). In a verbal condition, the trainee was required to determine whether the current stimulus letter matched another letter. In a spatial condition, the task was to determine whether or not stimuli matched in spatial location.

We first examined learning-effects in a data set from eight trainees (4 female) in which recordings were made with dense 115-channel arrays while they performed the spatial and verbal versions of the control and high load WM tasks for a total of about 350 trials in each condition. The trainees had performed several practice blocks of the task on a previous day, and so were not entirely naive. Examination of behavioral performance in the task revealed a marginal increase in accuracy $[F(7,1)=3.99, p<0.091]$ and a significant decrease in reaction time $F(7,1)=7.51, P<0.03]$ when contrasting a relatively naive state (the first 50 trials of each condition) with a highly practiced state (the last 50 trials of each condition). Parallel to these practice related effects were effects of task difficulty, with higher accuracy $[F(7,1)=23.63, p<0.002]$ and faster reaction times $[F(7,1)=42.95, p<0.001]$ in the control tasks than in the high load WM tasks. These factors were not involved in any interactions.

Examination of power spectra computed from the data suggested that practice most affected the EEG in the 3-7 Hz (theta) and 7-13 Hz (alpha) bands in most trainees, while a few trainees demonstrated more idiosyncratic practice-related EEG changes at higher and lower frequencies. Topographically, the theta band EEG changes were largely isolated to midline frontal recording sites. The alpha band changes were more widely distributed, but were most reliably observed over parietal and parieto-occipital sites. Practice was observed to increase both theta power [for peak frequency (average=6 Hz) at Fz: $F(7,1)=12.27, p<0.01$) and alpha power [for peak frequency (average=11 Hz) at POz, $F(7,1)=5.84, p<0.05$]. However, task difficulty had opposite effects in these two frequency bands. Specifically, frontal theta power was higher in the difficult WM tasks than in the control tasks $[F(7,1)=9.88, p<0.02]$, whereas alpha power was lower in the WM tasks than in the control tasks. Further, for the theta peak, there was a significant interaction between the task difficulty dimension and practice: theta increased with practice for the difficult WM tasks, but not for the control tasks $[F(7,1)=7.01, p<0.04]$. There were no interactions involving the alpha peak, and neither EEG measure was sensitive to the spatial versus verbal dimension of the study.

These differences in distribution and task correlates between the theta and alpha bands indicate that at least two types of EEG phenomena change in conjunction with practice related performance improvements in this demanding computer-based task. We suggest that as trainees practice the tasks their performance improves, their ability to effectively focus their attention (concentrate) on task performance increases (as reflected in the increase in frontal EEG theta band power) and they experience less overall neurocognitive (mental) workload (as reflected in the increase in alpha band EEG power).

Figure 2:
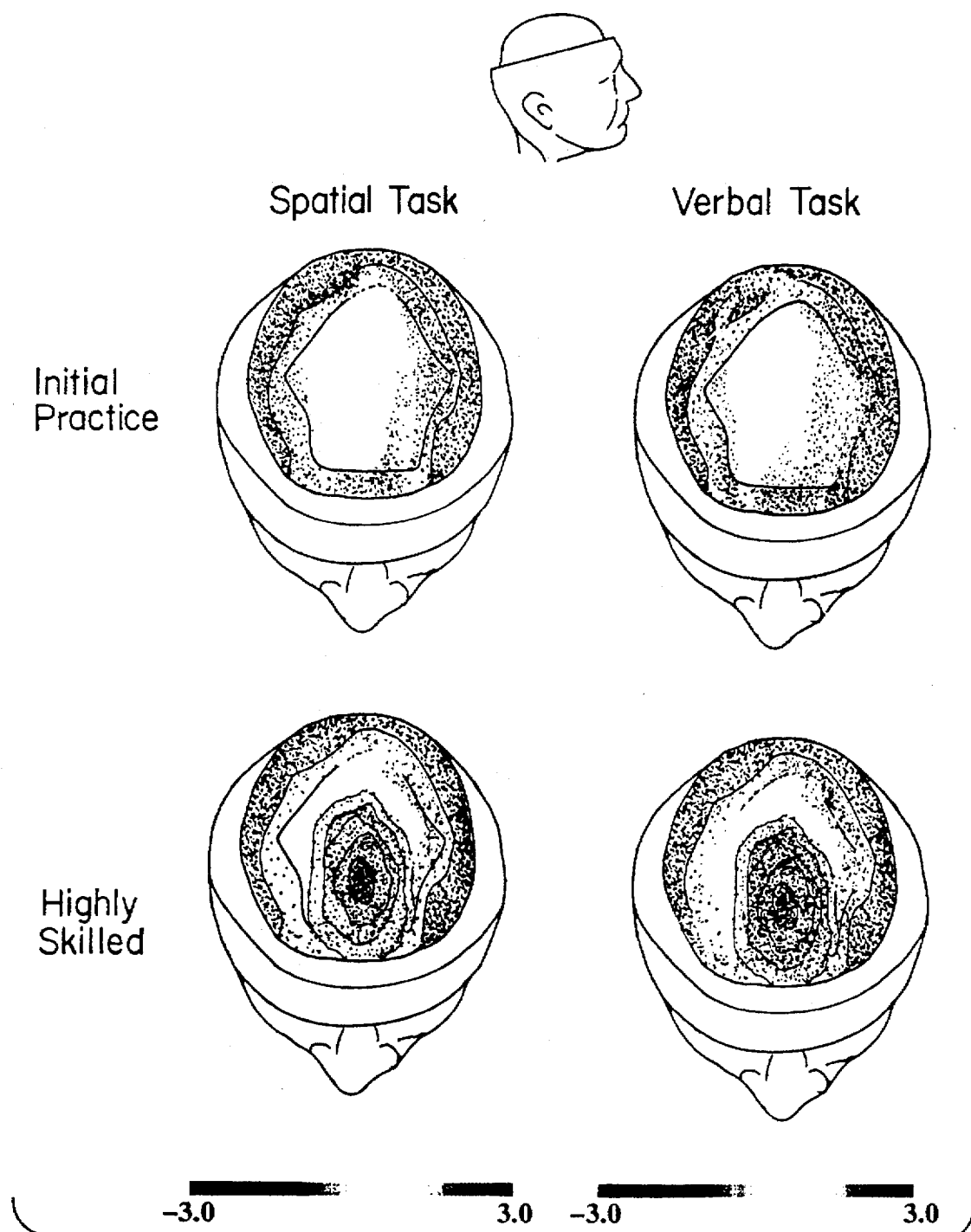
FIG. 2: Shows that frontal lobe EEG activity in the theta band increased as a trainee practiced spatial and verbal versions of a difficult working memory task. This is a neurological sign that the trainee's focused attention has increased after practicing the task.
Figure 3:
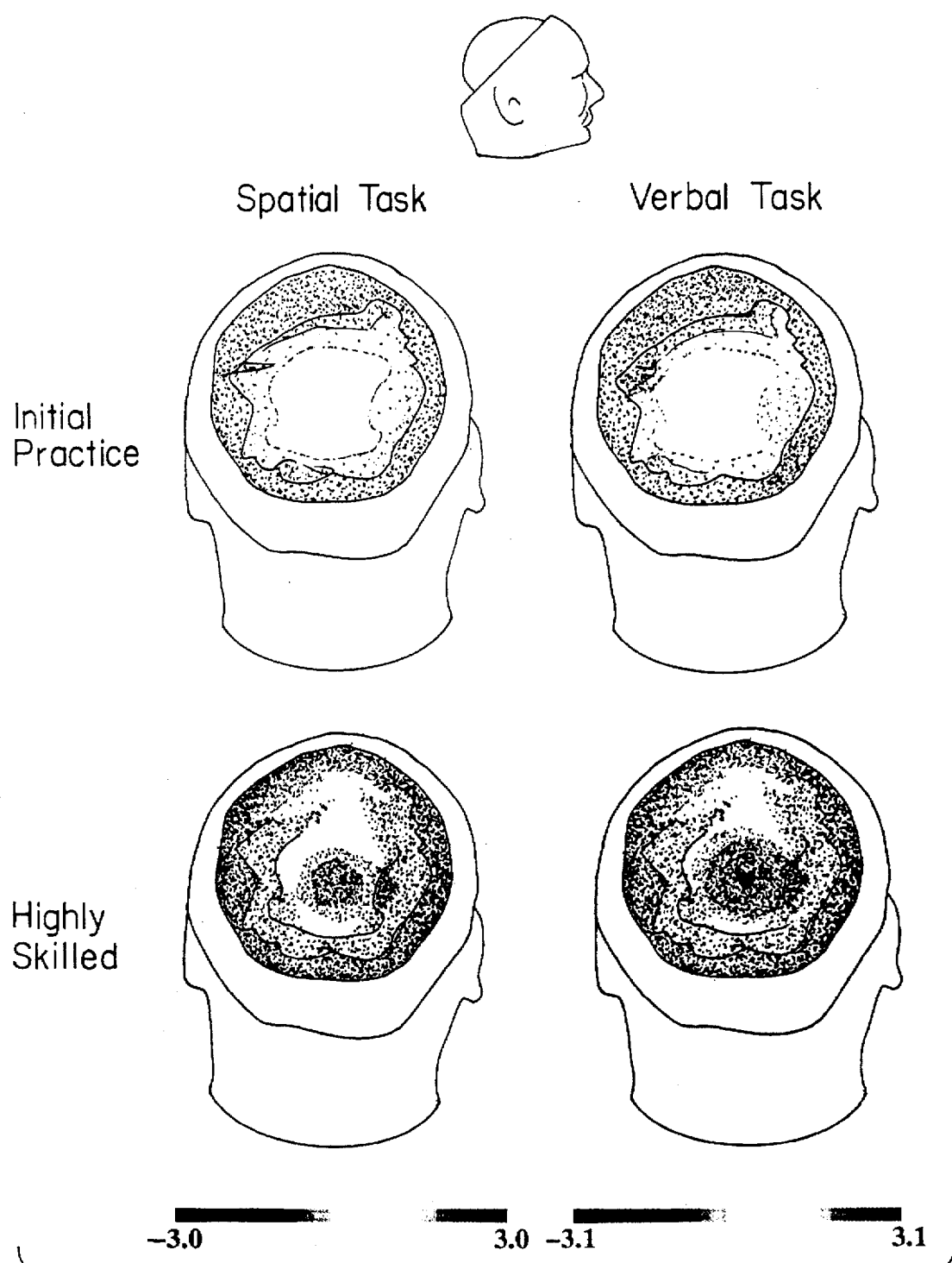
FIG. 3: Shows that parietal lobe EEG activity in the alpha band increased as a trainee practiced spatial and verbal versions of a difficult working memory task. This is a neurological sign that the trainee's neurocognitive workload has decreased after practicing the task.

In three trainees in whom these signals were largest, physiological data were registered with MRI-derived head models, and spatially enhanced with our Deblurring technique, described in U.S. Pat. No. 5,331,970, which uses geometrically realistic models of local variations of scalp and skull conductivity to estimate how brain electrical fields appear near the cortical surface. FIG. 2 portrays the estimated cortical topography and task correlates of the theta band activity, illustrating its restricted distribution in the midline frontal region, and its increase in amplitude in the WM tasks when the trainee is in a highly practiced state. Applying single equivalent current dipole modeling techniques to individual theta bursts to estimate the source of this EEG signal in data from each of three trainees, we found results consistent with a source for this signal in the anterior cingulate gyrus, an area which PET and lesion studies have implicated as an important component of an anterior attentional network critical to the performance of complex cognitive tasks. This result suggests that an important component of the acquiring skill in demanding tasks is the development of an effective strategy for focusing attention to relevant task dimensions. FIG. 3 illustrates the increase in alpha band EEG activity over the parietal lobe with practice of the WM tasks. The relative predominance of alpha activity during cognitive tasks has been hypothesized to be inversely proportional to the fraction of conical neurons recruited into a transient functional network for purposes of task performance; this hypothesis is consistent with the observation that alpha is attenuated by increases in task difficulty. The increase in alpha activity with practice, particularly given that it is associated with improvements in performance, suggests that trainees are learning to perform the tasks with greater "neural efficiency" That is, they appear to require less neural resources to perform the tasks after they have practiced them, and thus we suggest that an important sign of skill acquisition and automatization in demanding tasks is the reduction in neurocognitive workload.

We next investigated learning effects in a second experiment in which eight trainees performed eight runs of twenty trials in each of 6 task conditions (low, intermediate, and high difficulty versions of the spatial and verbal WM tasks described above), and this process was repeated on three separate days over the course of a week while their brain, eye and scalp muscle electrical signals were recorded from a 32 channel electrode montage. For purposes of the analysis of skill acquisition and automatization, we collapsed data across the spatial-verbal dimension, and focused on identifying changes in electrophysiological measures that were associated with practice on the most difficult level of the WM task during the first day of testing (exploratory analyses indicated that relatively little change in performance measures occurred over the course of the second two days of testing, suggesting that most of the task acquisition was occurring on day one).

Figure 4:
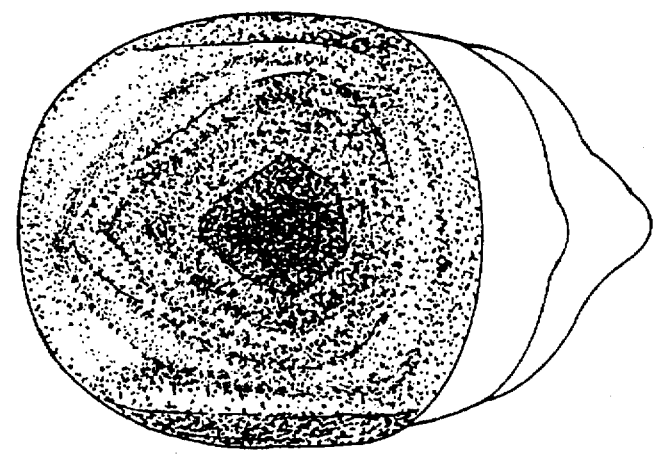
FIG. 4: Shows that frontal lobe EEG activity in the theta band gradually increased as a group of eight trainees practiced a difficult working memory task. This is a neurological sign that their focused attention increased as they practiced the task.
Figure 4:
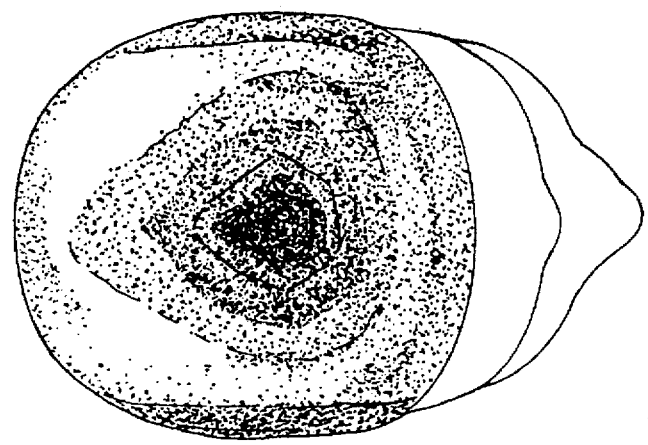
Figure 4:
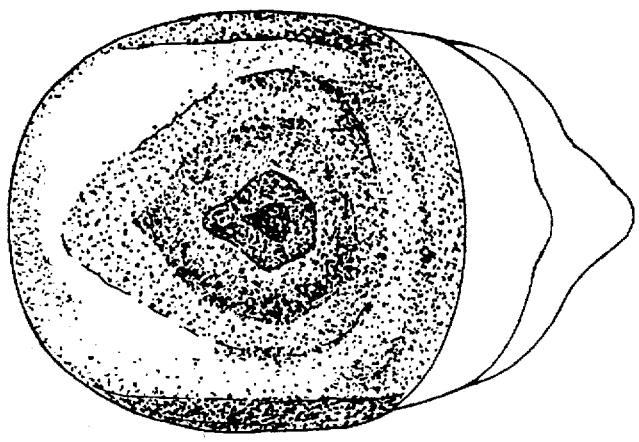
Figure 5:
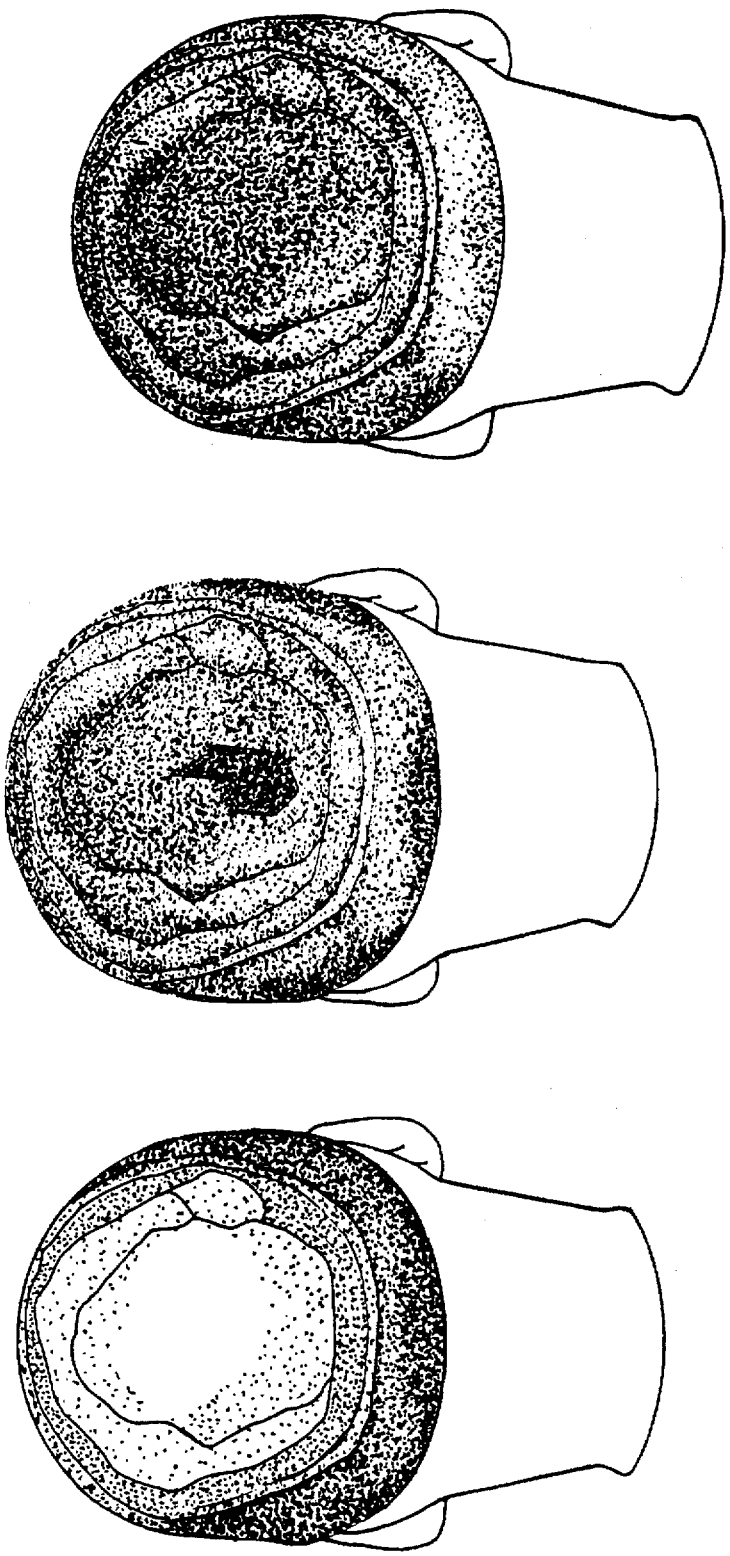
FIG. 5: Shows that parietal lobe EEG activity in the alpha band gradually increased as a group of eight trainees practiced a difficult working memory task. This is a neurological sign that their neurocognitive workload decreased as they practiced the task.

Data were grouped into naive (first two runs of the day for a total of 80 trials when collapsing across spatial-verbal dimension) and practiced (last two runs of the day) classes. Although target detection accuracy did not significantly differ between these two classes [F<1], reaction times were much faster in the practiced state than in the naive state [F(7,1)=14.8, p<0.006]. As in the prior dataset, practice was observed to increase both frontal theta (FIG. 4) power [for peak frequency (average=6.5 Hz) at Fz: F(7,1)=12.65, p<0.0] and alpha (FIG. 5) power [for peak frequency (average=10. Hz) at Pz, F(7.1)=14.8, p<0.0061], with some trainees displaying idiosyncratic practice-related changes in lower or higher frequencies. Further, many trainees also displayed practice related changes in scalp muscle tension. That is, broad band high-frequency (30–50 Hz) electromyographic (EMG) signals associated with tension in the temporoparietalis and occipitalis scalp muscles were often observed to decrease with practice.

To measure practice related changes in these signals, we first performed trainee-specific neural-network based EEG pattern recognition analyses, as described in U.S. Pat. No. 5,295,491 and patent application Ser. No.: 08/183,621, on these data to discriminate differences in EEG patterns between the naive and practiced states. For each trainee EEG and EMG power spectral features were computed to serve as inputs to a network, and the data were divided into training and testing sets with a 3:1 ratio respectively for both classes. Utilizing alpha, theta, and EMG signals, an average test set classification accuracy of 97% (range 96%–100%) was obtained across trainees. Thus, when trained on examples of a trainee's own electrophysiological signals recorded during task performance, it was possible to automatically determine from physiological signals alone whether a new data sample was recorded from the trainee when he or she was performing the WM task in a naive or practiced state (See Table 1).

Figure 6:
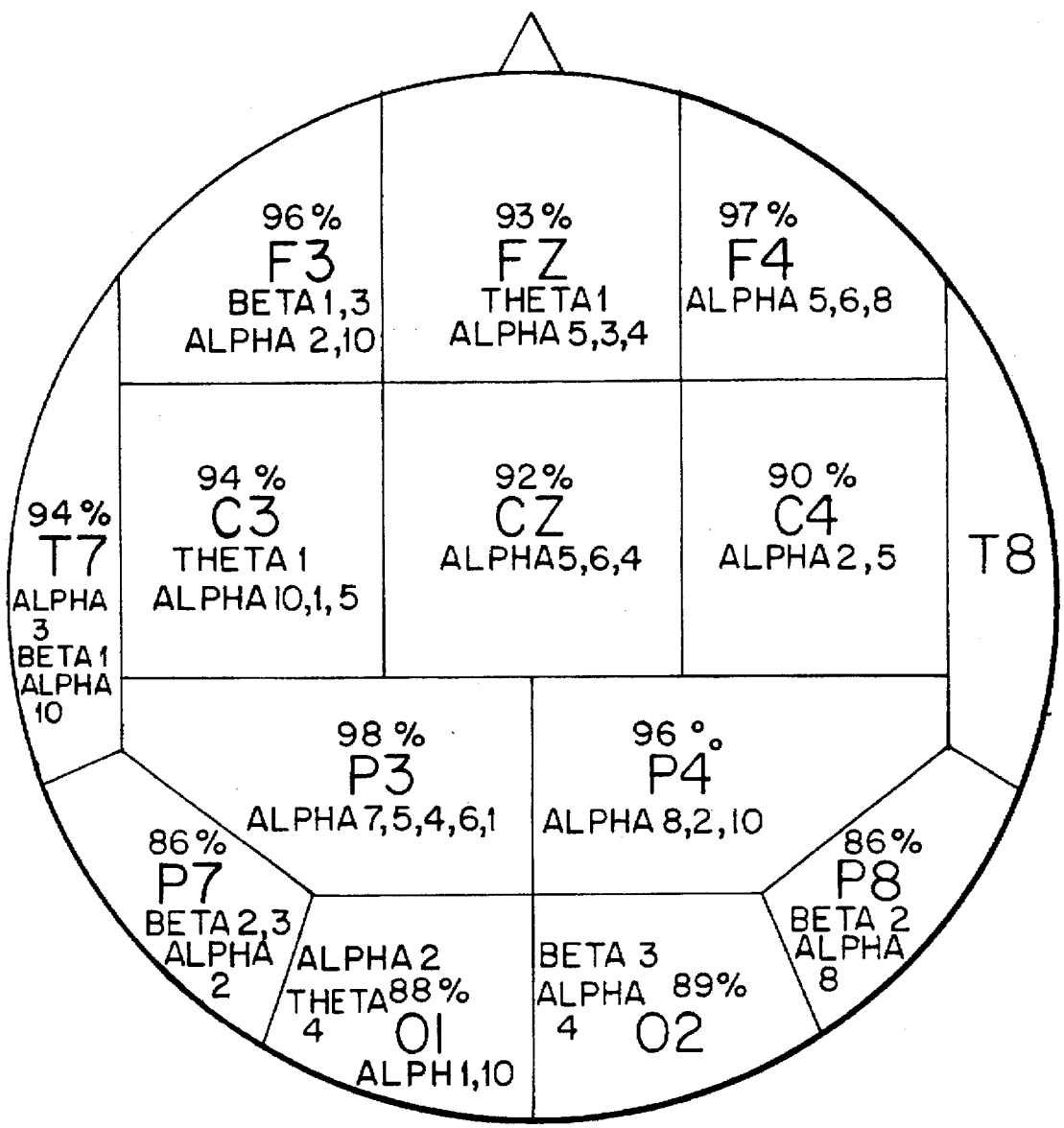
FIG. 6: Shows that training has a differential effect on different areas of the brain. The largest effects of learning the working memory task in this subject were recorded over the left and right frontal (96% and 97% classification accuracy) and left and right superior parietal (98% and 96%) areas. Practice of the task had a relatively smaller effect on the left and right occipital (88% and 89%) and left and right parieto-occipito-temporal junction (86% and 86%) areas. This pattern of regional brain utilization characterizes the neurocognitive strategy the trainee used to acquire skill in this task.

In order to characterize a trainee's neurocognitive strategy, a second analysis was performed which measured how different brain areas differed between the naive and practiced states. In this analysis, separate pattern recognition analyses were done for each of fourteen different regions, including left, mid and right frontal, left, mid and right motor, left and right temporal, left and right superior parietal and left and right parieto-occipito-temporal junctions. FIG. 6 shows the results of that analysis. It is evident that the left and right frontal and left and right superior parietal areas showed the largest effect of training (96–98% classification accuracy), with increases in a number of alpha and beta band EEG variables. The midline frontal area was slightly less effected by training (93%) with increases in theta and several alpha band EEG variables. By contrast, the parieto-occipito-temporal junction and occipital areas changed much less during the course of training (86–89%).

For automated methods for continuously measuring such changes, we next detected electrophysiological changes associated with practice by training a computer neural network on data from a group of individuals and applying it to data samples from an individual who wasn't part of the training group. For this analysis EEG and EMG power spectral features were computed to serve as inputs to the network, and the data from 7 of the trainees were used to train the network. The resulting network was then tested on data from the remaining trainee. This strategy was repeated across eight jackknives, allowing each trainee to serve as a test case. For this strategy to be successful there must be a high degree of similarity across trainees in the neurophysiological and physiological changes that occur with practice on a task. An average test accuracy of 89% was obtained across trainees (range 81%–97%) (see Table 2). Posterior alpha features were important contributors to all 8 of the resulting networks, temporoparietal EMG was an important feature in 7 of the networks, frontal midline theta was an important feature in 7 of the networks and frontal alpha was important in 4 of the networks. These results are remarkable in that they suggest that learning-related changes in the EEG and scalp EMG are highly reproducible and similar across trainees.

Acquisition and Analysis of Data From Subjects Learning the Space Fortress Task

We performed a third experiment in which the EEG was recorded from six right-handed trainees (mean age 23.3, range 22–25, 1 female), during acquisition of a complex and difficult flight simulator training task called "Space Fortress". Space Fortress is a video game-like task that has been studied intensively by the U.S. Air Force since it requires a representative analogue of the skills necessary for operating complex military aircraft and other systems. The task has also been used for many years in laboratories around the world as a research tool in basic studies of the mechanisms and processes of procedural learning and in applied studies aimed at developing optimal training strategies. Studies have suggested that the attentional skills developed during practice in the Space Fortress (SF) task can transfer to improvements in the actual flight performance of pilots.

In the standard SF task, the operator controls a spacecraft icon moving in a frictionless environment on the computer screen. It has second order control characteristics and has missiles to neutralize hostile elements. The major hostile element is the "Space Fortress" itself which can track and fire ordinance at the operator's craft. The other hostile factor are "mines" that appear at regular intervals. These mines can be either friendly or hostile; friend or foe classification requires utilizing information from working memory. The operator's objective is to maximize game points by destroying the fortress as many times as possible, destroying as many hostile mines as possible and protecting the ship from damage. Control panels indicate the current score and status of several variables. The training protocol we developed is a variant of the Multiple Emphasis on Components skill training strategy. Specifically we have initially focused on having trainees first practice mastering control of the spacecraft, where points were awarded when the craft is maintained within boundaries without crashing into obstacles (points related to ship control are indicated in a "control" gauge on the computer screen). Over a period of two days trainees performed eight sets of ten 2.5 minute runs in which they selectively tried to maximize their control scores without trying to destroy the fortress or mines. At the end of each such set they played one five-minute run where they sought to maximize the total score. Subjects were paid $10/hour for participation, and, to insure continued motivation, were given the opportunity to win a bonus payment based on high performance. Control and total scores were recorded for each block, and trainees made subjective ratings of task difficulty after each set. Thirty-two channels of EEG, eye-movement and scalp muscle data were collected simultaneously with each task run. Prior to other analyses these datafiles were processed using our artifact decontamination algorithms.

Figure 7:
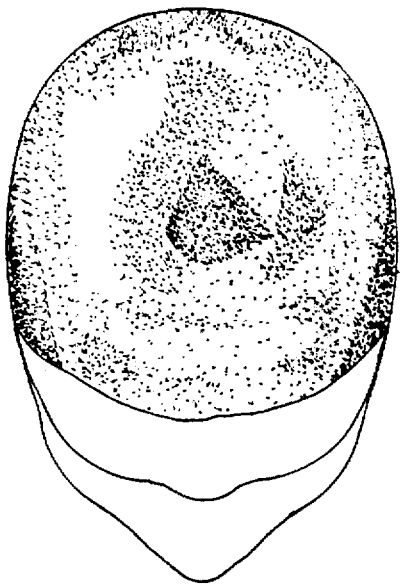
FIG. 7: Shows that frontal lobe EEG activity in the theta band increased as a group of six trainees practiced a difficult space flight simulator control task. This is a neurological sign that their focused attention increased as they practiced the task.
Figure 7:
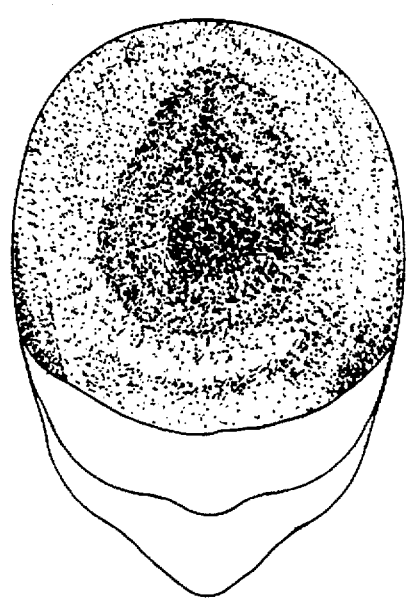
Figure 8:
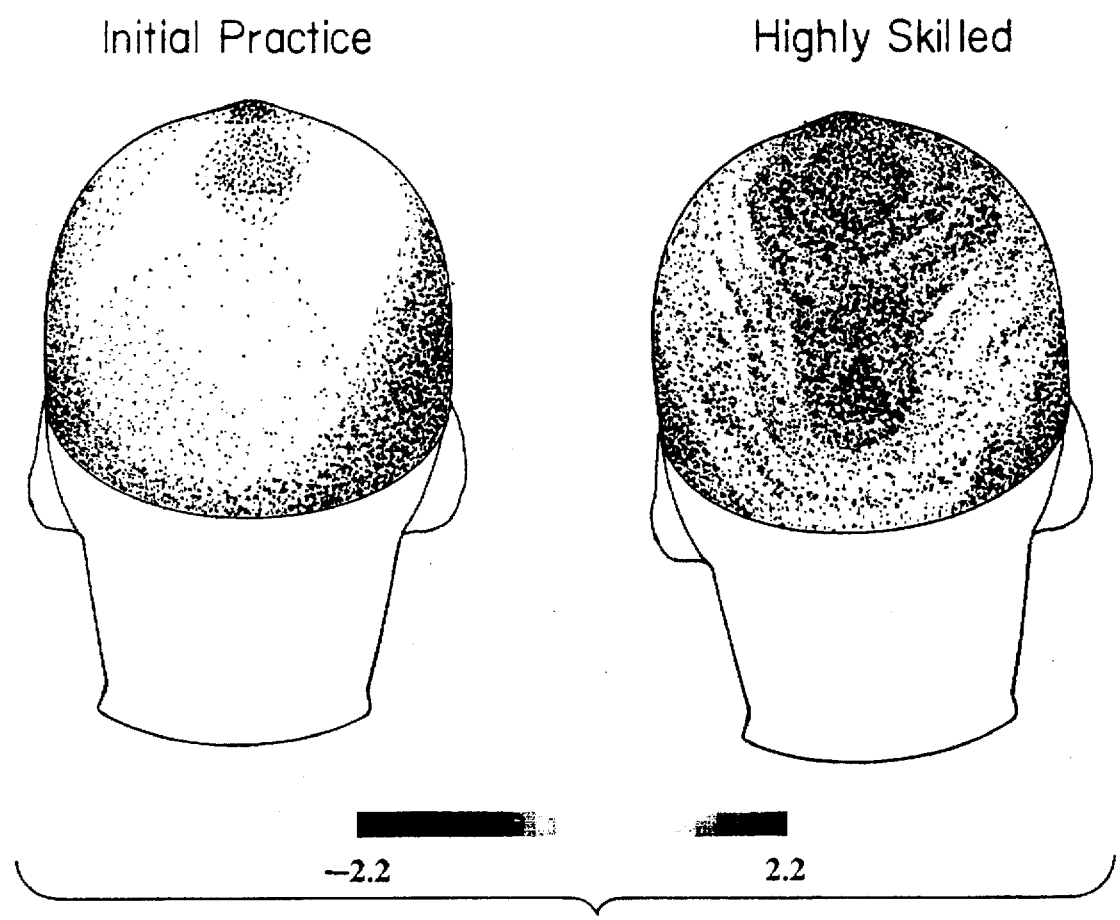
FIG. 8: Shows that widespread EEG activity in the alpha band gradually increased as a group of six trainees practiced a difficult space flight simulator control task. This is a neurological sign that their neurocognitive workload decreases as they practiced the task.
Figure 9:
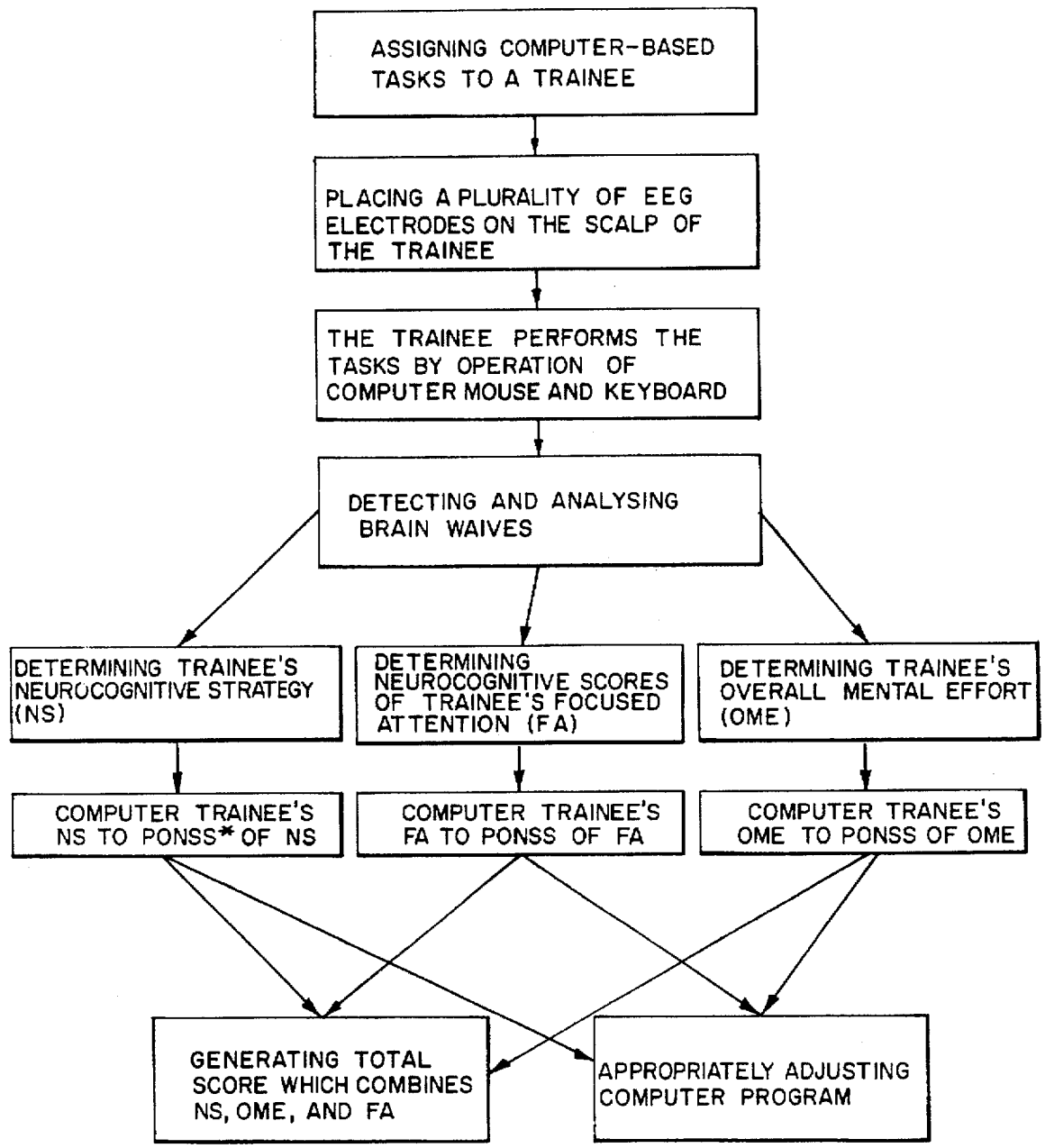
FIG. 9: A flow chart showing a preferred embodiment of the present invention.

Subjects displayed a significant increase in control scores during Space Fortress training from the first run in their first set of ten runs to the first run in their eighth set of ten runs [dependent $t(5)=-2.54$, one-tailed $p<0.01$]. However, subjective difficulty ratings did not significantly decrease over the same period [$t(5)=1.46$, $p>0.10$], suggesting that substantial mental effort was required for this activity, even after many hours of practice. As above, inspection of the spectral measures of the EEG revealed reliable practice-related increases in power in the theta (FIG. 7) band at midline locations over the frontal lobes [for peak frequency at Fz: $t(5)=-2.65$, one-tailed $p<0.03$], and in the alpha (FIG. 8) band at more widespread scalp locations [for peak frequency at Pz, $t(5)=-3.53$, one-tailed $p<0.01$]. As in the WM task, most trainees also demonstrated decreases in scalp muscle tension (EMG) as reflected in decreased power in a broad high frequency band (30–50 Hz) over lateral frontal, temporal, parietal, and/or occipital sites; several trainees displayed idiosyncratic changes in lower and higher frequency ranges (i.e. delta or beta band activity).

Subject-specific neural network pattern recognition analyses were performed on data segments from the first 10 (naive) and last 10 (practiced) training runs in each of the trainees. The data of each trainee were separated into 3 training and 3 testing sets (3:1 ratio of training to testing data). EEG features in combination with EMG features were first analyzed, then EEG features alone were analyzed separately to determine effects of practice on brain activity in isolation from other factors. The average classification performance across trainees for the 3 test data sets in the EEG/EMG analyses was 100%. The average test set classification performance utilizing EEG features alone (mainly frontal theta and regional alpha features) was 94% (range 86%–100%) (see Table 3).

Cross-task Generalization of EEG-Based Metrics of Task Acquisition

We have investigated how EEG pattern recognition networks trained to discriminate naive from practiced states in one task generalize to EEG collected while trainees practice other tasks. Illustrative results are shown for a trainee who performed the space fortress, working memory and superdivided attention training protocols on different days. The superdivided attention protocol (U.S. patent application Ser. No. 08/183,621. Filed Jan. 19, 1994, now U.S. Pat. No. 5,447,166. issued Sep. 5, 1995) requires learning how to do a complex divided attention task with concurrent immediate memory, immediate memory, dynamic visuospatial reasoning, and arithmetic reasoning components presented on different regions of a computer screen. In the immediate memory task, stimuli are presented continuously, and the trainee must compare the current stimulus with the immediately preceding stimulus, and make a "match" or "mismatch" button press response. In the dynamic visuospatial reasoning task the trainee must make a button press response at the appropriate time so that a "missile" fired from a stationary letter intercepts a target letter travelling vertically across the screen. In the arithmetic reasoning task, the trainee must mentally solve a simple mathematical equation and indicate with the appropriate button press, whether the outcome is greater or less than 5.

Theta band EEG power from frontal sites and alpha band EEG power from central and posterior sites were used to train a network to discriminate between naive and practiced performance of the difficult WM (working memory) task in the same fashion as described above, with average test set classification of 99% across jackknives. This network was then applied to naive and practiced data samples from this trainee's space fortress recording, and a 90% accurate classification was obtained. Finally, when the same network was applied to data from the complex divided attention task, 88% of data samples were correctly classified as coming from either the naive or practiced states. These results lend credence to the notion that general changes in the EEG accompany practice on a wide variety of different types of computer based tasks, and support the development of a general physiological metric for measuring the acquisition of difficult tasks.

SUMMARY AND CONCLUSIONS

These results are the first demonstration that EEG pattern recognition techniques can detect learning-related changes in brain state during the course of training exercises. The classification accuracies are among the highest we have ever seen in any of our studies. (The signals of practice are comparable in strength to the change in brain activity from eyes closed to eyes open.) The results support the viability of this technology for automatically assessing the degree of learning in the context of computer-based training exercises.

TABLE 1

Individual trainee neural network pattern recognition results in which the system classified previously unanalyzed Working Memory task data of a trainee into naive and well learned categories according to a previously computed mathematical function derived for that trainee.

| Trainee | Classification | Most Important Features |
| --- | --- | --- |
| S1 | 98% | ALP7, ALPZ, ALO1 |
| S2 | 90% | ALO1, ALP8, ALC3 |
| S3 | 98% | EMGT7, ALT7, ALP3 |
| S4 | 100% | EMGP7, ALFZ, ALPZ |
| S5 | 97% | EMGP7, EMGP8, EMGT7, ALP4 |
| S6 | 98% | EMGP8, EMGP7, ALO1, ALC3 |
| S7 | 97% | ALP8, EMGT7 |
| S8 | 96% | ALC4, ALP4, ALFZ |

Note: In the Tables AL is Alpha, TH is theta, EMG is electromyogram (30–50 Hz EEG). The electrode positions are O1 (left occipital), P8 (right lateral parietal), etc. in the conventional expanded 10–20 system of electrode placement.

TABLE 2

Group neural network pattern recognition results in which the system classified the Working Memory task data of a new trainee into naive and well learned categories according to a previously computed mathematical function derived from a group of trainees.

| Trainee | Classification | Most Important Features |
|---|---|---|
| S1 | 89% | ALC3, EMG P8, ALT7 |
| S2 | 90% | ALFZ, THFZ, ALP8 |
| S3 | 85% | EMGP8, ALC3, ALT7 |
| S4 | 93% | ALP8, EMGP8, ALT7 |
| S5 | 85% | ALP8, THFZ, ALFZ |
| S6 | 97% | ALT7, EMGP8, EMGT7 |
| S7 | 88% | EMGP8, EMGP7, THFZ |
| S8 | 81% | EMG P8, ALP8, ALC3 |

TABLE 3

Individual trainee neural network pattern recognition results in which the system classified previously unanalyzed Space Fortress task data of a trainee into naive and well learned categories according to a previously computed mathematical function derived for that trainee. The classification performance was 100% for each of the six trainees when both EEG and EMG signal features were used. The table shows the performance using EEG features only.

| Trainee | Classification | Most Important Signal Features |
|---|---|---|
| SF1 | 91% | THF4, THCZ |
| SF2 | 97% | ALOZ, THFZ |
| SF3 | 86% | THAF3, THF3, THFZ |
| SF4 | 90% | ALPZ, ALP4, ALO2 |
| SF5 | 100% | THFZ, THAF4, THF4 |
| SF6 | 98% | THF3, THAF4 |

Experiment To Measure Neurocognitive Workload

We designed an experiment to determine whether neural network based pattern recognition could use physiological features to distinguish between 3 levels of difficulty on a working memory task, whether these features would generalize across task versions that were matched on stimulus, response, and difficulty parameters, but that differed in the type of cognitive processing required (spatial versus verbal working memory), and whether these features were reliable enough to generalize across testing sessions.

Procedure

Eight healthy young adults (22–28 yrs, mean age 24 yrs; three females) participated as subjects. Subjects were recruited by advertisments placed in a local university employment center and were paid for their participation. All participation was fully informed and voluntary.

Subjects performed Working Memory tasks described in U.S. patent application Ser. No. 08/183,621. Filed Jan. 19, 1994. Neurocognitive Adaptive Computer Interface Method and System Based on On-Line Measurement of the User's Mental Effort, now U.S. Pat. No. 5,447,166, issued Sep. 5, 1995. In these tasks, stimuli were presented in a continuous sequence and the subject was required to compare the current stimulus with those earlier in the sequence. Each stimulus was selected from a set of twelve capital letters, and displayed in one of twelve screen positions. In a spatial load condition trainees were required to compare the current stimulus to either a constant stimulus (control task), the immediately preceding stimulus (low load WM task) (Working Memory), the stimulus that occurred two trials ago (intermediate load WM task), or the stimulus that occurred three trials ago (high load WM task). In a verbal condition, the subject was required to determine whether the current stimulus letter matched another letter. In a spatial condition, the task was to determine whether or not stimuli matched in spatial location. Subjects were thus required to remember the order of the stimuli as well as their identity or location. Trials were 4.5 seconds long, therefore, in the 2-back level subjects had to remember the information over 9 seconds whereas in the 3-back level, subjects had to retain each stimulus for 13.5 seconds.

Each subject participated in three experimental sessions, each lasting 6 to 8 hours. The first two sessions occurred on two consecutive days. The subjects then had one day off before the final session. On the first day, the experimental procedures were described to the subject and informed consent was obtained. The subject then performed the forwards and backwards digit span subtest of the WAIS-R and was given a brief description of the memory task prior to being prepared for the electrophysiological recordings. On the first day, the subject began by performing all the 6 tasks in order of increasing difficulty. Subjects then performed 7 repetitions of each of the 6 tasks. The tasks were presented in groups of 6, with each task occurring once within the group. The order of the task within the group was randomized. Subjects were given a lunch break and rest periods as needed. Electrophysiological data were recorded as subjects performed all the tasks. Data obtained during the initial group of 6 tasks each day were not used in the subsequent analyses. Data obtained from the first 3 trials of each task were also excluded from subsequent analyses, since in the 3-back level, no responses were required on this task. At the end of the final experimental session, subjects performed the Raven's Progressive Matrices test; electrophysiological measurements were not obtained during the performance of this test.

Subjects earned a bonus for good performance; they were given 5 cents for each correctly detected 'match' stimulus and lost 5 cents for each incorrect match response. Match stimuli occurred randomly on 50% of the trials. Subjects were instructed to respond as quickly and accurately as possible. Subjective ratings on difficulty were obtained after the performance of each task using the Subjective Workload Assessment Technique (SWAT). Subjective fatigue ratings were obtained after each group of 6 tasks using a 7 point scale with end points of "Extremely Alert" and "Extremely Tired".

EEG was recorded from 27 scalp locations (Fp1, Fp2, AF3, AF4, FT9, F7, F3, FZ, F4, F8, FT10, T7, C3, CZ, C4, T8, P9, P7, P3, PZ, P4, P8, P10, O1, OZ, O2, I) using a linked-mastoids reference. EOG activity was recorded from electrodes located above each eye, referenced to an electrode at the outer can thus of each eye. Physiological signals were sampled at 256 Hz, using a bandpass of 0.01 to 70 Hz. Raw EEG signals were fed into artifact-detection and correction programs, which detected both vertical and horizontal eye movements as well as blinks, and filtered them out of the EEG data. The data were then visually inspected to assess the performance of the artifact correction algorithm. Missed eye movements and blinks, instrumental noise and movement artifacts were deleted.

Statistical Results

Behavioral Results.

A Condition (verbal, spatial) by Level (1-back, 2-back, 3-back) by Day (1, 2, 3) repeated measures analyses of variance (ANOVA) on the percent correct scores yielded a significant effect of Level ($F(14,2)=51.54$; $p<0.001$). The Tukey Honestly Significant Difference (HSD) test showed that scores for the 1 and 2-back levels were significantly higher than scores for the 3-back level (97.4, 96.0, and 86.6% respectively). There was also a significant effect of Day ($F(14,2)=18.29$; $p<0.001$), with the Tukey HSD test showing significantly higher performance on Days 2 and 3 compared with Day 1 (90.6, 94.6, 94.8% for Days 1, 2, and 3 respectively). The Level by Day interaction was significant ($F(28,4)=15.28$; $p<0.001$); in simple effects ANOVAs, Day did not have a significant effect on the performance in the one-back tasks, but significantly affected both 2- and 3-back task performance (1-back: $F(14,2)=0.76$; $p>0.05$; 2-back: $F(14,2)=10.91$; $p<0.01$; 3-back: $F(14,2)=17.90$; $p<0.001$).

The Condition by Level by Day ANOVA on the d' scores revealed a significant Level effect ($F(14,2)=49.36$; $p<0.001$), with the 3-back level generating significantly lower scores than the 2 and 1-back levels (2.69, 3.82, and 4.13, respectively). There was also a significant Day effect ($F(14,2)=6.66$; $p<0.05$); scores on Day 1 were significantly lower than those on Days 2 and 3 (3.23 verus 3.69 and 3.73 respectively). The Day by Level interaction was significant ($F(28,4)=4.76$; $p<0.05$). Simple effect ANOVAs showed that for the 1-back level, scores did not significantly change across days whereas for the 2- and 3-back levels, scores increased across days, being significantly higher on days 2 and 3 than on day 1.

For reaction time, the Condition by Level by Day ANOVA showed a significant effect of Level ($F(14,2)=29.16$; $p<0.001$). The Tukey HSD test showed that reaction times were significantly faster in the 1-back than in the 3-back condition (676, 817, and 907 ms for 1-, 2-, and 3-back tasks, respectively). There was also a significant Day effect ($F(14,2)=16.69$; $p<0.01$), with reaction times being significantly slower on Day 1 than on Days 2 and 3 (947, 765, 689 ms for day 1, 2 and 3 respectively). There were no significant effects of Condition, nor any significant interaction effects.

We also analyzed the reaction time variance using the standard deviation obtained from all correct responses in each 20-trial block. This ANOVA showed a significant effect of Level ($F(14,2)=20.41$; $p<0.01$), with 1-back tasks eliciting significantly smaller reaction time standard deviations than the 2- and 3-back tasks (182.3, 234.0, 270.4 ms for 1-, 2-, and 3-back levels, respectively). There was also a significant effect of Day ($F(14,2)=7.70$; $p<0.05$), with the standard deviation decreasing across days, being significantly smaller on Day 3 than on Day 1 (270.5, 219.2, and 197.5 ms, for day 1, 2, and 3 respectively).

Subjective measures of mental workload was also assessed, with each of the three SWAT questions were analyzed separately. The first SWAT question pertained to time load, the second to mental effort load, and the third to psychological stress load. For all questions, there was a main effect of level, with higher levels eliciting higher ratings (Swat 1: $F(14,2)=6.09$; $p<0.05$; 1.19, 1.36, 1.57 for 1- 2-, and 3-back respectively; Swat 2: $F(14,2)=18.77$; $p<0.01$; 1.32, 1.58, 1.95 for 1-, 2-, and 3-back respectively; Swat 3: $F(14,2)=6.06$; $p<0.05$; 1.34, 1.27, 1.53, for 1-, 2-, and 3-back respectively). For question 1, there was also a significant effect of Day, with scores decreasing across days ($F(14,2)=4.14$; $p<0.05$; 1.49, 1.41, 1.22 for Days 1, 2, and 3 respectively).

In sum, analysis of the behavioral and subjective data indicate that the experimentally-defined workload levels did indeed differ in difficulty. Both reaction time and accuracy showed significant effects of workload level with subjects showing a monotonic increase in reaction time and decrease in accuracy from the lowest to the highest workload level. The SWAT measures indicated that subjects found the three levels to significantly differ in difficulty, with the lowest level being the easiest and the highest level the hardest. No significant differences were observed between the verbal and spatial versions of the tasks. These anlayses also indicated that significant learning occurred in the difficult task conditions over the three days of testing. For current purposes, analyses of physiological data will primarily focus on recording performed after the task had been learned, i.e. primarily of day 3 of the study, and on the +1 month retest data.

Electrophysiological Data.

For initial examination of this data set, EEG topography was spatially enhanced with a Laplacian transform utilizing realistic head shape information derived from the measured electrode positions on each individual subject. Log power spectra for the ongoing EEG were then computed over a 9 second interval with a 4-second window and a 1 second hop. Following visual inspection of the data, integrated energy measurements were obtained from the log of the power spectra for each subject in the alpha, beta, theta and EMG bands and subjected to conventional statistical analyses.

At central sites in the theta band a Condition by Level by Site (Fz, Cz, Oz, Pz) ANOVA revealed a significant site effect ($F(21,3)=26.80$; $p<0.001$), with largest values occurring over Fz. There was also a significant site by level effect ($F(42,6)=6.00$; $p<0.01$). At Fz, theta increased with difficulty level; at Cz, Pz, and Oz, theta decreased with difficulty level. This decrease in theta band activity with task difficulty at more posterior sites most likely reflects overlap with posterior alpha activity, which also showed this decrease in power with increasing task difficulty (see below). Thus subsequent theta analyses were restricted to frontal sites. Across frontal sites, a Condition by Level by Site (F3, Fz, F4) ANOVA showed a significant Condition effect ($F(7,1)=7.63$; $p<0.05$) with Verbal tasks producing higher theta than Spatial tasks (4.23 versus 4.03 10 log microvolt squared). This difference between spatial and verbal tasks likely also reflect overlap with broad-band alpha activity, that is (as described below) Spatial tasks produced more attenuation of alpha activity that did Verbal tasks.

At central sites in the alpha band a Condition by Level by Site (Fz, Cz, Pz, Oz) ANOVA revealed a significant site effect ($F(21,3)=12.15$; $p<0.001$) with largest alpha occurring at parietal and occipital areas. The level effect was also significant ($F(14,2)=10.67$; from the lowest alpha decreasing from the lowest to the highest workload level (5.65, 4.55, 2.95 10 log microvolt squared, for the 1-, 2-, and 3-back levels respectively.—Tukey HSDs showed a significant difference between 1 and 3-back levels only.). The Condition effect approached significance ($F(7,1)=4.95$; $p=0.061$) with Spatial tasks attenuating alpha more than verbal tasks (4.59 vs. 4.18). At lateral sites a Condition by Level by Hemisphere by Site (AF3, F3, C3, T7, P3, P7, O2, and the corresponding sites over the right hemisphere) ANOVA showed a significant site effect ($F(42,6)=15.79$; $p<0.001$), again with alpha increasing from frontal to posterior sites; the largest alpha occurred over the occipital electrodes. There was also a significant level effect, ($F(14,2)=15.74$; $p<0.01$) with alpha decreasing with increasing difficulty level (6.60, 5.60, and 4.08 10 log microvolt squared, for 1-, 2-, and 3-back tasks respectively) (Tukey HSD comparisons showed a significant difference between 1 and 3-back levels). The Condition effect approached significance, ($F(7,1)=5.47$; $p=0.052$), again with Spatial tasks attenuating alpha more than Verbal tasks (5.62 vs. 5.25). The Site by Condition effect was significant ($F(42,6)=3.97$; $p<0.05$). Unvariable post-hoc ANOVAs revealed significant condition effects at parietal sites only. At the P3, P4 site, alpha in the Verbal condition exceeded that in the Spatial condition by 1.1 10 log microvolt squared (F(7,1)=8.21; p<0.05). At P7, P8, Verbal alpha exceed Spatial alpha by 0.53 10 log microvolt squared (F(7,1)=7.04; p<0.05). At occipital sites, Verbal alpha was larger than Spatial alpha by 0.7 10 log microvolt squared, but this difference failed to reach significance (F(7,1)=4.52; p=0.071). There was no significant difference between Verbal and Spatial alpha at frontal, central, or temporal sites. There was also a significant Site by Level interaction (F(4,12)=5.23; p<0.05). All univariate post hoc ANOVAs were significant (i.e. there were level effects at all sites, and site effects for all levels). The Hemisphere by Condition effect was significant (F(7,1)= 9.08; p<0.05): over the fight hemisphere, alpha in the Verbal task was significantly higher than in the spatial task F(7,1) =9.08; p<0.05; 6.19 vs. 5.62 10 log microvolt squared). There was no significant difference between Verbal and Spatial alpha over the left hemisphere (5.04 and 4.87 10 log microvolt squared for Verbal and Spatial respectively).

At central sites in the Beta band, a Condition by Level by Site (Fz, Cz, Pz, Oz) ANOVA showed a significant Level effect (F(14,2)=16.42; p<0.001), with largest beta occurring in the easiest levels (-2.81, -3.21, -3.91 10 log microvolt squared for 1-, 2-, and 3-back respectively). At lateral sites, a Condition by Level by Hemisphere by Site (AF3, F3, C3, T7, P3, P7—and the corresponding sites over the fight hemisphere) ANOVA showed a significant Level effect (F(14,2)=12.02; p<0.01): Beta decreased with difficulty level (0.16, 0.02, and -0.43 10 log microvolt squared for 1-2- and 3-back respectively). There was also a significant Site effect (F(35,5)=4.28; p<0.05); Beta was largest over the temporal (T7 and T8) areas. Given that these electrodes fall over the temporoparietalis muscle, enhanced Beta band activity at these electrodes might primarily reflect contributions from scalp EMG. This is evidenced by the fact that when EMG band activity was submitted to a Condition by Level by Hemisphere by Site (P7/8, T7/8) ANOVA a significant Site effect was obtained (F(7,1)=27.90; p<0.01), with largest EMG occurring over the temporal sites. Although in some subjects EMG power reliably discriminated between workload levels, this effect was not reliable enough to be significant in group analyses.

In sum, conventional statistical analyses of these data indicated that theta activity at frontal sites tended to increase with increasing task difficulty workload levels. Current evidence is consistent with a source for this signal in the anterior cingulate gyrus, an area by implicated by PET and lesion studies and intracranial recordings as an important component of an anterior attentional network critical to the performance of complex cognitive tasks. Conversely, alpha (and to a lesser extent beta) band activity tended to decrease with increases in task difficulty. The magnitude of alpha activity during cognitive tasks has been hypothesized to be inversely proportional to the fraction of cortical neurons recruited into a transient functional network for purposes of task performance (Gevins & Schaffer, 1980); this hypothesis is supported by the observation made here of monotonic alpha attenuated associated with progressive increases in task difficulty.

Pattern Recognition Results

The conventional statistical analyses described above established that the experimental manipulations were sufficient to significantly vary task difficulty as measured objectively by performance and subjectively by personal report. They also established that this manipulation of task difficulty resulted in significant changes in spatiotemporal features of the EEG. To examine the feasibility of developing automated methods for continuously measuring practice related changes in these signals, we next trained neural network based pattern classification algorithms with samples of data from different workload levels, and then tested the resulting classifiers on new data samples from each task condition. The results of these pattern classification exercises are described below. Unless otherwise specified data samples were collapsed across the Spatial/Verbal dimension. This served to increase the size of the data set available for training and testing networks, and increased the generality of the resulting classifiers; however, to the extent to which small differences existed in the neural responses to these different task conditions the resulting classification scores probably underestimate what would have been obtained with data samples from homogenous experimental conditions.

Subject-Specific Analyses

In exploratory analyses we first performed subject-specific neural-network based EEG pattern recognition analyses on these data to discriminate differences in EEG patterns between the high and low workload states (i.e. 3-back vs. 1-back tasks). For each subject EEG and EMG power spectral features were computed on the data to serve as inputs to a network; the data were then divided into training and testing sets with a 3:1 ratio respectively for both classes. Excluding one outlier subject whose performance on the test day suggested that he wasn't making an effort to perform the task correctly, an average correct classification on test samples of 98% was obtained. We next tried to perform a substantially more difficult classification, discriminating the intermediate workload level from the high level (2-back vs 3-back tasks) and the intermediate level from the low level (2-back vs 1-back tasks). Average accuracies of 80% and 88% were obtained. A summary of the results for each subject, and the EEG features that best discriminated between mental workload levels, is provided in Table 4. Thus, when trained on examples of a subject's electrophysiological signals recorded during task performance, it was possible to automatically determine, with a high degree of accuracy, on a new data sample from the subject when he or she was performing an easy, moderately difficult, or extremely difficulty WM task.

Reliability and Generality

To examine the test-retest reliability of these subject specific mental workload indices, 4 of the 8 subjects returned for a fourth recording session 1–2 months after the end of the three sessions described above. For these subjects pattern recognition networks were trained on data samples from the same testing day as described above. We then examined how these networks would classify data taken from the retest testing sessionm, and obtained an average test set classification 95% (range 92%–99%). In subjects with enough data to permit it, we have also begun to examine whether networks trained on data samples from one task condition (e.g. in the "Spatial" task) generalize to classify data samples collected during the other task conditions. In the one subject in whom this approach has been applied (sub3 from Table 1), 100% accuracy was obtained for test data samples when discriminating the 3-back from the 1-back WM conditions.

Generalizability Across Subjects

To further examine the feasibility of developing automated methods for continuously measuring such changes, we next attempted to create a mechanism for detecting electrophysiological changes associated with high workload levels by training a network on data from a group of individuals and applying it to data samples from an individual who wasn't part of the training group. For this analysis EEG spectral features were computed from the 1-back and 3-back test conditions to serve as inputs to the network, and the data from 6 of the subjects were used to train the network. The resulting network was then tested on data from the remaining subject. This strategy was repeated across seven jackknives (excluding the outlier subject mentioned above), allowing each subject to serve as a test case. For this strategy to be successful there must be a high degree of similarity across subjects in the neurophysiological and physiological changes that occur with practice on a task. An average test accuracy of 84% was obtained across subjects. These results are quite remarkable in that they suggest that changes in the EEG related to mental workload are highly reproducible and similar across subjects. They are the first demonstration that a generic (group) EEG pattern recognition network can successfully be applied to a new subject to determine whether he or she is in a high mental workload state within the context of a specific task.

Extensions To More Naturalistic Tasks

As a further extension of our methods, we obtained a dataset recorded at Wright Patterson Air Force Base from a Air National Guard pilot operating a realistic KC-130 transport simulator, and applied our single subject pattern recognition approach to discriminate samples of baseline data from samples of data while the pilot was engaged in a simulated assault landing. Utilizing alpha band features we obtained over 95% test set accuracy in discriminating between data segments from high and low task difficulty levels. While preliminary, these initial results suggest that it may be possible to transition these measures to actual operational contexts.

CONCLUSIONS

These studies illustrate the feasibility of employing neural network-based pattern recognition techniques on combinations of physiological features in order to derive sensitive and reliable inferences about the mental workload of individual subjects. The EEG features which discriminated between workload levels are consistent with general measures of concentration that have been reported in a range of other task situations (see above), suggesting that they may have a high degree of generality.

TABLE 4

Individual subject neural network pattern recognition results in which the system classified previously unanalyzed Working Memory task data of a subject into low (1), medium (2) and difficult (3) mental workload levels according to a previously computed mathematical function derived for that trainee.

| TOP FEATURES | AVERAGE ACCURACY |
|---|---|
| SUB3 | |
| 1vs3: THFZ,ALF3,BETP3 | 100% |
| 1vs2: THFZ,ALP3,ALC3 | 95% |
| 2vs3: BETP3,THFZ,ALAF4 | 90% |
| SUB4 | |
| 1vs3: ALF4,ALP3,ALP4 | 99% |
| 1vs2: ALO2,ALP4,ALO1 | 91% |
| 2vs3: ALF4,ALO2 | 72% |
| SUB5 | |
| 1vs3: ALP3,ALT7,ALO2 | 96% |
| 1vs2: THAF4,ALP3,THFZ | 86% |
| 2vs3: ALP3,BETP8,ALO2 | 89% |
| SUB6 | |
| 1vs3: ALO1,BETT7,BETF3 | 96% |

TABLE 4-continued

Individual subject neural network pattern recognition results in which the system classified previously unanalyzed Working Memory task data of a subject into low (1), medium (2) and difficult (3) mental workload levels according to a previously computed mathematical function derived for that trainee.

| TOP FEATURES | AVERAGE ACCURACY |
|---|---|
| 1vs2: ALO1,BETF3,BETT7 | 94% |
| 2vs3: ALO2,BETF3,ALO1 | 68% |
| SUB7 | |
| 1vs3: ALF3,BETT8,ALFZ | 97% |
| 1vs2: ALP4,ALPZ,ALCZ | 74% |
| 2vs3: ALF3,BETT8 | 83% |
| SUB8 | |
| 1vs3 ALO2,THFZ | 98% |
| 1vs2: ALO2,ALP4,ALP3 | 89% |
| 2vs3 ALO1,BETP4,ALP7 | 74% |
| SUB10 | |
| 1vs3: ALPZ,ALO1,BETPZ | 100% |
| 1vs2: ALCZ | 89% |
| 2vs3: ALPZ,SLP8,ALP4 | 83% |

REFERENCES

Gevins, A. S. (1980) Pattern recognition of brain electrical potentials. *IEEE Trans. Patt. Anal. Mach. Intell.*, PAMI-2 (5), pp. 383–404.

Gevins, A. S., Bressler, S. L., Cutillo, B. A., Illes, J., Miller, J., Stern, J., Jex, H. (1990) Effects of prolonged mental work on functional brain topography. *EEG clin. Neurophysiol.*

Gevins, A. S. and Cutillo, B. A. (1993) Spatiotemporal dynamics of component processes in human working memory. *Electroenceph. Clin. Neurophysiol.*, Vol. 87, Elsevier: Amsterdam, pp. 128–143.

Gevins, A. S., Cutillo, B. A., and Smith, M. E. (1995) Regional modulation of high resolution evoked potentials during verbal and nonverbal matching tasks. *Electroenceph. Clin. Neurophysiol.*, 94, Elsevier: Amsterdam, pp. 129–147.

Gevins, A. S., Smith, M. E., et al. (Submitted) Subsecond Dynamics of Cortical Networks Subserving Human Working Memory. *EEG clin. Neurophysiol.*

Gevins, A. S. and Morgan, N. H. (1986) Classifier-directed signal processing in brain research. *IEEE Trans. Biomed. Eng.*, BME-33 (12), pp. 1054–1068.

Viglione, S. S. (1970), "Applications of pattern recognition technology," In: J. M. Mendel & K. S. Fu, *Adaptive Learning and Pattern Recognition Systems*, New York: Academic Press.

What is claimed is:

1. A method in computer based training of a human trainee for a computer to automatically assess learning related changes in the trainee's brain state, including the steps of:

(a) presenting the trainee with a battery of learning tasks in which the trainee operates the computer using a muscle operated computer input control means;

(b) while the trainee performs the learning tasks, detecting and analyzing the brain waves of the trainee with an EEG (electroencephalograph) device having at least one electrode removably connected to the trainee to determine neurocognitive scores of the trainee's focused attention;

(c) comparing the trainee's scores of focused attention with previously obtained normal score standards of focused attention; and (d) automatically adjusting a portion of a learning program being run by the computer if the trainee's on-line neurocognitive scores of focused attention are a predetermined amount below or above a threshold value based upon the previously obtained normal score standards of focused attention.

2. A method as in claim 1 wherein the previous obtained normal score standards of focused attention are obtained for the same tasks, or for a battery of standard learning calibration tasks, either from the same trainee or from a group of similar trainees.

3. A method as in claim 2 wherein the trainee's on-line neurocognitive workload scores includes the trainee's overall mental effort scores and the normal score standards includes an overall mental effort score.

4. A method as in claim 3 wherein the overall mental effort score is measured by weighted combinations of power, crosspower, coherence and phase angle of individual frequency components, of the whole band and at peak frequency, and by parameters of parametric models, in the 7–13 Hz (alpha) and 13–26 Hz (beta) EEG bands recorded from electrodes over the entire cerebral cortex, in the 3–7 Hz (theta) band recorded over parietal, temporal and occipital cortex, and in higher frequency bands (greater than 26 Hz) recorded over temporalis, occipitalis and frontalis muscles.

5. A method as in claim 1 and also detecting and analyzing the brain waves to determine overall mental effort (neurocognitive workload) scores of the trainee while the trainee performs the learning tasks; comparing the trainee's overall mental effort scores with the previously obtained normal score standards of overall mental effort from the same trainee or from a group of similar trainees performing the same learning tasks or performing a battery of standard learning calibration tasks; and adjusting a portion of a learning program being run by the computer if the trainee's on-line neurocognitive scores of overall mental effort are a predetermined amount below or above a threshold value based upon the previously obtained normal score standards of overall mental effort.

6. A method as in claims 1, 2 or 5 and automatically assessing a type of neurocognitive strategy (differential degrees of utilization of brain systems associated with perception, action and cognition) the trainee is using to perform the learning tasks by scoring and analysis of the trainee's brain wave frequencies and amplitudes at each electrode compared to the previously obtained normal score standards of brain wave frequencies and amplitudes; and adjusting a portion of a learning program being run by the computer if the trainee's neurocognitive strategy differs by a predetermined amount from the previously obtained normal score standards of brain wave frequencies and amplitudes.

7. A method as in claims 1, 2 or 5 wherein the adjustment of the program is an adjustment in timing when a next learning task is presented.

8. A method as in claims 1, 2 or 5 wherein the adjustment of the program is an adjustment between visual and auditory modalities.

9. A method as in claims 1, 2 or 5 wherein the adjustment of the program is within the visual modality between linguistic and graphical types of displayed information.

10. A method as in claims 1, 2 or 5 wherein the adjustment of the program is within the auditory modality between verbal and non-verbal types of information presented.

11. A method as in claims 1, 2 or 5 wherein the adjustment of the program changes the content of information presented.

12. A method as in claims 1, 2 or 5 wherein the adjustment of the program is to not present information to the trainee which otherwise would have been presented.

13. A method as in claims 1, 2 or 5 wherein the adjustment of the program is to present information to the trainee which otherwise would not have been presented.

14. A method as in claims 1, 2 or 5 wherein the trainee views and listens to selected training tasks but is not required to respond to the selected training tasks using muscle operated computer input control means.

15. A method as in claims 2 or 5 in which the battery of standard learning calibration tasks is selected from the group of working memory, divided attention, visuomotor and tracking tasks.

16. A method as in claims 1, 2 or 5 wherein the computer executes a pattern recognition algorithm and the method includes the step of training the algorithm to extract the neurocognitive scores selected from the group of focused attention, mental effort and strategy corresponding to stages of skill acquisition, neurocognitive automatization and learning strategy.

17. A method as in claim 16 in which the pattern recognition algorithm is selected from the group of a neural network algorithm, a fuzzy logic algorithm, a genetic learning algorithm, a statistical pattern classification algorithm, a syntactic pattern classification algorithm, a Bayesian or entropy (information) based cluster analysis algorithm, and a combination of the aforesaid algorithms.

18. A method as in claim 16 using the pattern recognition algorithm to separately extract neurocognitive scores of focused attention, mental effort and strategy.

19. A method as in claim 16 using the pattern recognition algorithm to generate a single function containing scores of neurocognitive focused attention, overall mental effort and strategy.

20. A method as in claim 16 and the step of training the pattern recognition algorithm using data generated by the trainee.

21. A method as in claim 16 and the step of training the pattern recognition algorithm using data generated by the group.

22. A method as in claim 16 and the step of adjusting a group pattern classification function previously derived from a group using the trainee's scores to adjust the group function to a trainee.

23. A method as in claim 1, 2 or 5 and wherein the trainee's neurocognitive scores (focused attention, mental effort or strategy) are compared to threshold values based upon standard values in the neurocognitive literature.

24. A method as in claims 1, 2 or 5 and making the comparisons using a pattern recognition algorithm in which the trainee's data are compared with generic learning patterns derived from a normal population performing the same learning task or a battery of standard learning calibration tasks, or with learning patterns derived from the trainee performing the same learning task or a battery of standard learning calibration tasks.

25. A method as in claim 24 wherein a specific score is obtained for each trainee by transforming each trainee's brain wave data to Z-score variables using the statistical distribution of the trainee's initialization data and subsequent data, and inputting the Z-score variables into the pattern recognition algorithm.

26. A method as in claims 1, 2 or 5 and placing a hat, head set or holder having a plurality of at least two electrodes on the trainee's head with the electrodes in contact with the scalp of the trainee while the trainee performs the learning tasks.

27. A method as in claim 5 wherein the portion of the program is adjusted to a less difficult training level if the trainee's overall mental effort score is above a threshold value.

28. A method as in claim 5 wherein the portion of the program is adjusted to a more difficult level if the trainee's overall mental effort score is below a threshold value.

29. A method as in claims 1, 2 or 5 wherein the portion of the program being run is changed depending on the trainee's use of specialized brain systems involved with perception, action, and cognition which includes: planum temporale, superior temporal gyrus, Heschl's gryus and associated structures involved with auditory processing and speech perception; occipital and inferotemporal cortices and parieto-occipito-temporal junction and associated structures involved in visual processing and pattern recognition; precentral gyrus, lateral premotor cortex, supplementary motor cortex, and associated structures involved with planning, initiation and execution of motor movements; dominant hemisphere frontal operculum, dorsolateral, orbitofrontal and mediobasal frontal cortex, and planum temporale and supramarginal gyrus and associated structures involved with language functions and networks of structures encompassing the anterior and posterior cingulate, hippocampus, hippocampal gyrus, and prefrontal, parietal, and temporal association cortices and associated regions involved in processing spatial information, in preparation and sequential planning, in reasoning, in focusing and shifting attention in learning and in working memory.

30. A method as in claim 1 wherein the neurocognitive scores of (b) includes the trainee's on-line overall neurocognitive scores of focused attention and the previously obtained normal score standards of focused attention of (c) includes overall on-line neurocognitive focused attention scores.

31. A method as in claim 30 wherein the overall neurocognitive score of focused attention is measured by weighted combinations of power, crosspower, coherence and phase angle of individual frequency components, of the whole band, and at peak frequency, and by parameters of parametric models, in the 3–7 Hz (theta) and 7–13 Hz (alpha) EEG bands recorded from electrodes over the prefrontal cortex.

32. A method as in claim 1 wherein the neurocognitive scores of focused attention of (b) includes on-line neurocognitive normal score standards of focused attention of the trainee for each of a plurality of specialized brain systems and the normal score standards of focused attention of (c) includes normal scores for standards of focused attention for each of the specialized brain systems.

33. A method as in claim 1 wherein the portion of the program is adjusted to a more difficult training level if the trainee's neurocognitive focused attention score is above a threshold value.

34. A method as in claim 1 wherein the portion of the program is adjusted to a more difficult or less difficult level if the trainee's neurocognitive focused attention score is below a threshold value.

35. A system in computer based training of a human trainee in which the computer runs a plurality of programs to automatically assess learning related changes in the trainee's brain state without the trainee exerting muscle command action, including:

(a) a computer having computer memory and muscle operated input means to operate the computer;

(b) means for presenting the trainee with a battery of learning tasks involving the trainee operating the input means;

(c) means for detecting and analyzing the brain waves of the trainee comprising an EEG (electroencephalograph) device having a plurality of electrodes removably connected to the scalp of the trainee to determine neurocognitive scores of focused attention for the trainee while the trainee performs the learning tasks, and means for recording the trainee's focused attention scores comprising a portion of the computer memory;

(d) means in the computer memory for storing previously obtained normal score standards of focused attention;

(e) means in the computer for comparing the trainee's scores with the normal score standards; and (f) means in the computer for automatically adjusting a portion of a program being run by the computer as determined by the comparison, if the trainee's on-line score is a predetermined amount below or above a threshold.

36. A system as in claim 35 and further including means for detecting and analyzing the trainee's brain waves to determine the trainee's on-line overall mental effort scores (neurocognitive workload) while the trainee performs the learning tasks; means for storing normal score standards of overall mental effort; means in the computer for comparing the trainee's on-line overall mental effort scores with the stored normal score standards of overall mental effort; and means in the computer for automatically adjusting a portion of a learning program being run on the computer if the trainee's on-line neurocognitive scores of overall mental effort based on said comparison are a predetermined amount below or above a threshold value.

37. A system as in claims 35 or 36 wherein the normal score standards are obtained from a battery of standard calibration tasks or the same learning tasks and from the same trainee or from a group of similar trainees.

38. A system as in claims 35 or 36 and means for simultaneously detecting and measuring other physiological signals of the trainee while the trainee is performing the learning tasks, said signals being selected from the group of facial muscle, eye muscle, heart activity and respiration.

39. A system as in claim 36 wherein the trainee's on-line neurocognitive workload scores include the trainee's overall neurocognitive mental effort scores and the normal score standards include an overall neurocognitive mental effort score.

40. A system as in claim 36 wherein the trainee's on-line mental effort scores include neurocognitive mental effort scores for each of a plurality of specialized brain systems and the normal score standards of mental effort includes a score for each of the specialized brain systems.

41. A system as in claims 35 or 36 and including a pattern recognition means for making the comparisons in which the trainee's data are compared with generic learning patterns derived from a normal population performing the same learning tasks or a battery of standard learning calibration tasks, or with learning patterns derived from the trainee performing the same learning tasks or a battery of standard learning calibration tasks.

42. A system as in claim 41 and including means for obtaining a specific calibration for each trainee by transforming each trainee's brain wave data to Z-score variables using the statistical distribution of the trainee's initialization and subsequent data, and inputting the Z-score variables into the pattern recognition means.

43. A system as in claims 35 or 36 and including a hat, headband or holder having a plurality of at least two electrodes to contact the scalp of the trainee.

44. A system as in claims 35 or 36 wherein the portion of the program is adjusted to a more difficult training level if the trainee's neurocognitive focused attention score is above a threshold.

45. A system as in claims 35 or 36 wherein the portion of the program is adjusted to a less or more difficult level if the trainee's neurocognitive focused attention score is below a threshold.

46. A system as in claim 35 or 36 wherein the portion of the program is adjusted to a less difficult training level if the trainee's overall mental effort score is above a threshold.

47. A system as in claim 35 or 36 wherein the portion of the program is adjusted to a more difficult level if the trainee's neurocognitive overall mental effort score is below a threshold.

48. A system as in claims 35 or 36 wherein the portion of the program being run is changed depending on the trainee's use of regional brain systems involved with perception, action, and cognition which include: planum temporale, superior temporal gyrus, Heschl's gyrus and associated structures involved with auditory processing speech perception; occipital and inferotemporal cortices and parieto-occipito-temporal junction and associated structures involved in visual processing and pattern recognition; precentral gyrus, lateral premotor cortex, supplementary motor cortex, and associated structures involved with planning, initiation and execution of motor movements; dominant hemisphere frontal operculum, dorsolateral, orbitofrontal and mediobasal frontal cortex, and planum temporale and supramarginal gyrus and associated structures involved with language functions; and networks of structures encompassing the anterior and posterior cingulate, hippocampus, hippocampal gyrus, and prefrontal, parietal, and temporal association cortices and associated regions involved in processing spatial information, in preparation and sequential planning, in reasoning, in focusing and shifting attention in learning and in working memory.

49. A system as in claim 35 wherein the focused attention scores of (c) include on-line overall neurocognitive focused attention scores and the normal standards of focused attention of (d) include overall normal standard neurocognitive focused attention scores.

50. A system as in claim 35 wherein the focused attention scores of (c) includes on-line neurocognitive focused attention scores for each of a plurality of specialized brain systems and the normal standard neurocognitive focused attention scores of (d) include a score for each of the specialized brain systems.

* * * * *